United States Patent
Moriya

(10) Patent No.: US 8,423,571 B2
(45) Date of Patent: Apr. 16, 2013

(54) MEDICAL IMAGE INFORMATION DISPLAY APPARATUS, MEDICAL IMAGE INFORMATION DISPLAY METHOD, AND RECORDING MEDIUM ON WHICH MEDICAL IMAGE INFORMATION DISPLAY PROGRAM IS RECORDED

(75) Inventor: Yoshiyuki Moriya, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 229 days.

(21) Appl. No.: 12/882,784

(22) Filed: Sep. 15, 2010

(65) Prior Publication Data

US 2011/0066635 A1  Mar. 17, 2011

(30) Foreign Application Priority Data

Sep. 16, 2009  (JP) ................. 2009-214231

(51) Int. Cl.
  *G06F 7/00*  (2006.01)
  *G06F 17/30*  (2006.01)
(52) U.S. Cl.
  USPC ........................................... 707/769
(58) Field of Classification Search .................. 707/769, 707/999.003
  See application file for complete search history.

(56) References Cited

U.S. PATENT DOCUMENTS

| 5,940,527 | A | 8/1999 | Takeo |
| 7,046,833 | B2 | 5/2006 | Masumoto et al. |
| 7,058,210 | B2 | 6/2006 | Mundy et al. |
| 7,348,582 | B2 | 3/2008 | Hasegawa |
| 7,546,154 | B2 | 6/2009 | Hornegger et al. |
| 7,899,684 | B2 | 3/2011 | Fukatsu et al. |
| 2005/0226405 | A1* | 10/2005 | Fukatsu et al. ............. 380/1 |
| 2008/0027889 | A1 | 1/2008 | Zhou et al. |
| 2009/0087048 | A1 | 4/2009 | Takahashi |

FOREIGN PATENT DOCUMENTS

| JP | 08-215183 A | 8/1996 |
| JP | 2001-137230 A | 5/2001 |
| JP | 2001-283191 A | 10/2001 |
| JP | 2003-271924 A | 9/2003 |
| JP | 2003298451 A | 10/2003 |
| JP | 2004-141612 A | 5/2004 |
| JP | 2008-043564 A | 2/2008 |
| JP | 2008-093254 A | 4/2008 |
| JP | 2008-253293 A | 10/2008 |
| JP | 2009-045286 A | 3/2009 |

OTHER PUBLICATIONS

European Search Report, Appln. No. 10176598.0-2201/2306355; Sep. 5, 2011.

(Continued)

*Primary Examiner* — Aleksandr Kerzhner
(74) *Attorney, Agent, or Firm* — Sughrue Mion, PLLC

(57) ABSTRACT

Image observation reports and medical images are displayed correlated to each other. A second keyword group is obtained, by detecting phrases that match keywords of a first keyword group that represent organs or pathologies from within image observation reports. The organs or pathologies represented by the first keyword group are automatically detected from within medical images, and a third keyword group that includes keywords corresponding to the detected organs or pathologies is obtained. Common keywords that match among keywords within the second and third keyword groups are obtained. Link data that correlates the organs or pathologies corresponding to the common keywords are generated for each common keyword. The common keywords and indicia that represent the organs or pathologies corresponding to the common keywords are displayed correlated to each other.

13 Claims, 14 Drawing Sheets

OTHER PUBLICATIONS

Image Content Extraction: Application to MR Images of the Brain; Sinha, et al.; Inforad; XP-002430027; Mar.-Apr. 2001; RG vol. 21. No. 2: pp. 535-547.

Text Mining in Radiology Reports; Gong, et al. 2008 Eighth IEEE International Conference on Data Mining; pp. 815-820.

H. Fujita, et al., "Intelligent Computer-aided Diagnosis Based on Normal Structure Recognition of Human Body," Journal of 4th Symposium, "Computer Aided Diagnosis of Multi Dimensional Medical Images," Specified Area Research Funded by the Ministry of Education, Culture, Sports, Science and Technology, 2007, pp. 55-60.

K. Kubota, et al., "Evaluation of Computer-Aided Diagnosis system for Lung Cancer based on Helical CT images," Technical Report of the Institute of Electronics, Information and Communication Engineers, MI2001-41, 2001, pp. 41-46.

S. Kido, et al., "Intelligent CAD for diffuse lung diseases," Journal of 4th Symposium, "Computer Aided Diagnosis of Multi Dimensional Medical Images," Specified Area Research Funded by the Ministry of Education, Culture, Sports, Science and Technology, 2007, pp. 45-54.

Y. Wakida, et al., "Liver Cancer Detection based on a Temporal Density Feature from Abdominal Dynamic X-ray CT Images," Journal of Computer Aided Diagnosis of Medical Images, 2007, pp. 1-10, vol. 10, No. 1.

\* cited by examiner

FIG.10

| ORGAN A LIST |
|---|
| RIGHT UPPER LOBE : HIGH DENSITY REGIONS WITHIN RIGHT UPPER LOBE S1… |
| LEFT LOWER LOBE : HIGH DENSITY REGIONS WITHIN LEFT LOWER LOBE… … |

150A — RIGHT UPPER LOBE
150B — LEFT LOWER LOBE
150

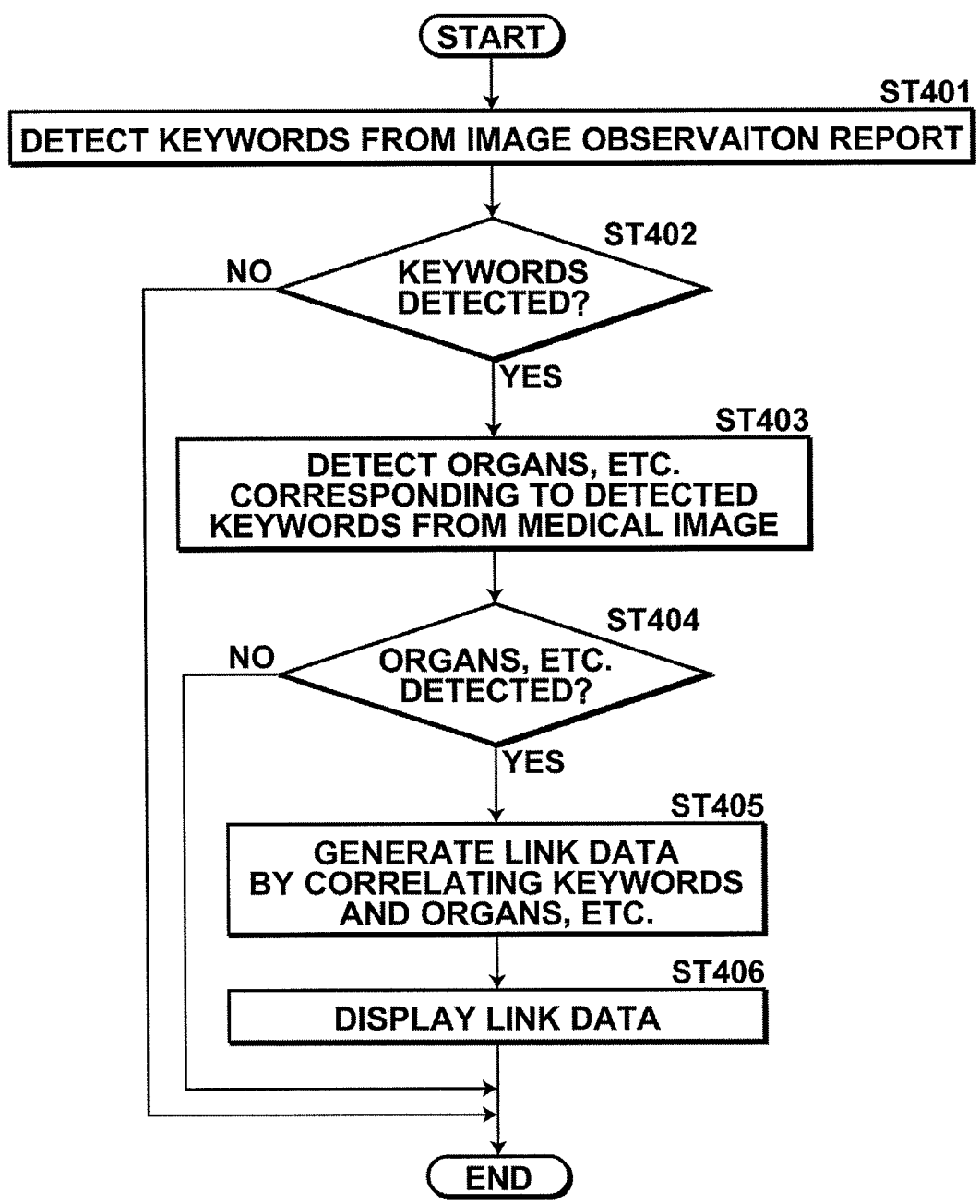

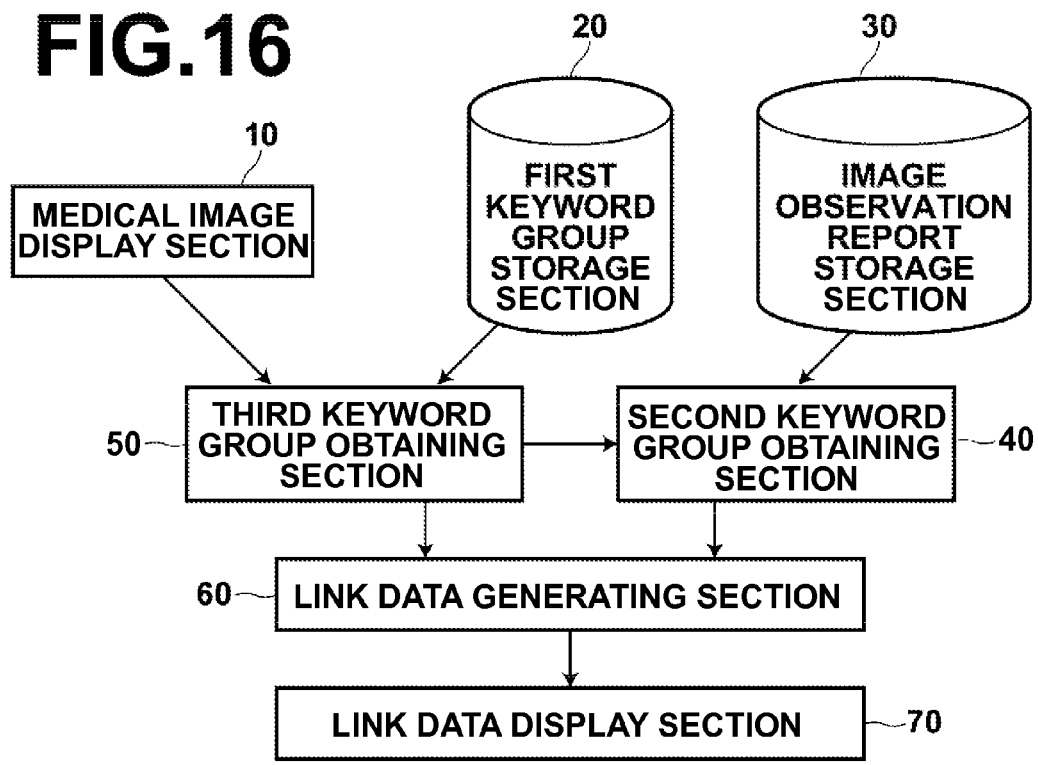

MEDICAL IMAGE INFORMATION DISPLAY APPARATUS, MEDICAL IMAGE INFORMATION DISPLAY METHOD, AND RECORDING MEDIUM ON WHICH MEDICAL IMAGE INFORMATION DISPLAY PROGRAM IS RECORDED

BACKGROUND OF THE INVENTION

1. Field of the Invention

The present invention is related to a medical image information display apparatus, a medical image information display method, and a medical image information display program.

2. Description of the Related Art

Recently, technologies for automatically detecting pathologies in organs using CAD (Computer Aided Diagnosis) have been developed in the field of medical image diagnosis. Accordingly, it has become possible to accurately assess and display diseased reasons or organs having the pathologies. In the technique described in Japanese Unexamined Patent Publication No. 2009-045286, a main branching structure is extracted from a medical image that represents the lung field, to determine the anatomical names of pulmonary segments. In the technique described in Japanese Unexamined Patent Publication No. 2008-093254, bone regions are extracted from tomographic images of a subject, and a projection image of the subject's bones are overlapped onto the tomographic images and displayed, to accurately assess the location of a nidus within the tomographic images, based on the positional relationship between the nidus and the bones.

Physicians and other diagnosticians perform diagnoses based on medical images that display organs extracted in this manner, and record the diagnostic results into electronic image observation reports.

However, in these conventional techniques, the contents of the image observation reports and pathologic regions within the medical images are not correlated. Therefore, it is necessary for physicians to search for pathologic regions within the medical images, when confirming pathologies described in the image observation reports. Conversely, it is also necessary to search for descriptions within image observation reports that correspond to pathologies within medical images, when referring to the image observation reports. That is, a burden exists that physicians need to assess the correspondent relationships between image observation reports and medical images.

Meanwhile, image observation reports, in which reference images are linked to text within image observation reports by hyperlinks, exist, as disclosed in U.S. Pat. No. 7,899,684 B2. In this type of image observation report, it is easy to understand the correspondent relationship between image observation reports and medical images. However, a burden exists that troublesome linking operations, in which text portions within the image observation report are selected from among a great number of choices and the reference images are dragged and dropped onto the text portions, are necessary.

SUMMARY OF THE INVENTION

The present invention has been developed in view of the foregoing circumstances. It is an object of the present invention to provide a medical image information display apparatus that correlates image observation reports and medical images in a simple manner and displays the correlated information on the medical images, to facilitate understanding of the correspondent relationships between medical images and image observation reports.

A medical image information display apparatus of the present invention is characterized by comprising:

medical image display means, for obtaining and displaying medical images;

image observation report storage means, for storing image observation reports related to the medical images;

first keyword group storage means, for storing a first group of keywords that include one of keywords that represent organs and keywords that represent pathologies;

second keyword group obtaining means, for detecting phrases that match the stored first group of keywords from within the image observation reports, and for obtaining a second group of keywords that include the detected phrases;

third keyword group obtaining means, for automatically detecting the organs and pathologies represented by the stored first group of keywords from within the medical images, and for obtaining a third group of keywords that include keywords corresponding to the detected organs and pathologies;

link data generating means, for comparing the second keyword group and the third keyword group, obtaining common keywords that match between the two groups, and for generating link data, in which each of the obtained common keywords are each correlated with the organs and pathologies that the common keywords correspond to; and link data display means, for displaying the common keywords, correlated with indicia that represent the organs and pathologies corresponding to the common keywords.

A medical image information display method of the present invention is characterized by comprising the steps of:

obtaining and displaying medical images;

storing image observation reports related to the medical images;

storing a first group of keywords that include one of keywords that represent organs and keywords that represent pathologies;

detecting phrases that match the stored first group of keywords from within the image observation reports and obtaining a second group of keywords that include the detected phrases;

automatically detecting the organs and pathologies represented by the stored first group of keywords from within the medical images and obtaining a third group of keywords that include keywords corresponding to the detected organs and pathologies;

comparing the second keyword group and the third keyword group, obtaining common keywords that match between the two groups, and generating link data, in which each of the obtained common keywords are each correlated with the organs and pathologies that the common keywords correspond to; and displaying the common keywords, correlated with indicia that represent the organs and pathologies corresponding to the common keywords.

A medical image information display program of the present invention is characterized by causing a computer to function as:

medical image display means, for obtaining and displaying medical images;

image observation report storage means, for storing image observation reports related to the medical images;

first keyword group storage means, for storing a first group of keywords that include one of keywords that represent organs and keywords that represent pathologies;

second keyword group obtaining means, for detecting phrases that match the stored first group of keywords from within the image observation reports, and for obtaining a second group of keywords that include the detected phrases;

third keyword group obtaining means, for automatically detecting the organs and pathologies represented by the stored first group of keywords from within the medical images, and for obtaining a third group of keywords that include keywords corresponding to the detected organs and pathologies;

link data generating means, for comparing the second keyword group and the third keyword group, obtaining common keywords that match between the two groups, and for generating link data, in which each of the obtained common keywords are each correlated with the organs and pathologies that the common keywords correspond to; and link data display means, for displaying the common keywords, correlated with indicia that represent the organs and pathologies corresponding to the common keywords.

Here, the "keywords that represent organs" from among the "keywords that represent organs and keywords that represent pathologies" include the names of organs, epithets associated with the organs, symbols that represent the organs, and abbreviations thereof. In addition, the "keywords that represent pathologies" include the names of diseases, epithets associated with the diseases, symbols that represent the diseases, and abbreviations thereof. For example, "lung", "liver", "bone", and "heart" may be employed as keywords that represent organs. Likewise, keywords that represent diseases include "lung cancer", "liver cell carcinoma", "liver cysts", "hepatic hemangioma", "bleeding in the liver region", "bleeding in the brain region", "abnormal patterns", "calcifications", "abnormal blood vessels", and interstitial lung diseases such as "consolidation", "Ground Glass Opacity (GGO)", "Crazy Paving", "honeycomb patterns", "emphysema patterns", and "nodular patterns".

Here, the "detected organs and pathologies" may be detected as points that indicate the positions of the organs and pathologies, or may be detected as regions that indicate diseased regions.

The expression "automatically detecting" refers to detecting organs or pathologies from medical images by CAD (Computer Aided Diagnosis) image processes.

A configuration may be adopted, wherein:

the link data generating means further correlates phrases that precede and follow the common keywords within the image observation reports to the link data in addition to the common keywords; and the link data display means displays the phrases that precede and follow the common keywords in addition to the common keywords.

It is preferable for the third keyword group obtaining means to designate keywords that represent the narrowest concept as the keywords corresponding to the organs and pathologies, in the case that the same organs and pathologies are detected based on a plurality of the keywords.

It is desirable for the second keyword group obtaining means to designate phrases that represent the narrowest concept as the detected phrases, in the case that a plurality of phrases that represent the same organ are detected within the image observation reports.

Here, the expression "represent the narrowest concept" refers to keywords and phrases that represent smaller sections of the same organ or pathology. For example, among the keywords that represent the lungs, "lungs", "right lung", "right upper lobe", and "right upper lobe S1" represent progressively narrower concepts.

A configuration may be adopted, wherein the medical image information display apparatus of the present invention further comprises:

image observation report display means, for displaying the image observation reports; and common keyword specifying means, for specifying the common keywords; wherein:

the link data generating means links the common keywords displayed by the link data display means to the common keywords within the image observation reports by hyperlinks; and the image observation report display means displays the entirety of the image observation reports in response to specification of the common keywords displayed by the link data display means, with the specified common keywords being displayed in an emphasized manner compared to other text within the image observation reports.

The expression "displayed in an emphasized manner" refers to displaying the specified common keywords such that they are distinguishable from non specified text, by known techniques such as coloring the specified common keywords, coloring the backgrounds of the specified common keywords, underlining the specified common keywords, causing the specified common keywords to blink, displaying the specified common keywords in bold type, changing the font of the specified common keywords, changing the size of the font of the specified common keywords, and providing frames around the specified common keywords.

The expression "specifying the common keywords" refers to specifying text that represents the common keywords with a mouse, keyboard, or other input device.

A configuration may be adopted, wherein the medical image information display apparatus of the present invention further comprises:

list display means, for displaying a common keyword list that includes a plurality of common keywords; wherein:

the link data display means displays indicia that represent an organ or a pathology corresponding to a specified common keyword, in response to specification of the specified common keyword from among the plurality of common keywords displayed in the common keyword list.

A configuration may be adopted, wherein:

the second keyword group obtaining means obtains the second group of keywords from a plurality of image observation reports regarding the same patient; and the link data generating means further correlates image observation report specifying data that specifies image observation reports that include the common keywords with the link data.

The expression "image observation report specifying data that specifies image observation reports" refers to data that clearly indicates which image observation report is specified in the case that a plurality of image observation reports are present. Examples of the image observation report specifying data include file names of image observation reports, and the dates on which the image observation reports were generated.

A configuration may be adopted, wherein:

the link data generating means correlates the common keywords included in the newest image observation report from among the plurality of image observation reports and image observation report specifying data that specifies the newest image observation report with the link data, when phrases corresponding to the same common keywords are detected within the plurality of image observation reports.

The link data generating means may generate an image observation report list that includes image observation report specifying data that specify a plurality of image observation reports when phrases corresponding to the same common keywords are detected within the plurality of image observation reports, and link the image observation report specifying data included in the image observation report list and the same common keywords included in the image observation reports corresponding to the image observation report specifying data by hyperlinks; and the list display means may further display the image observation report list.

A configuration may be adopted, wherein:

the third keyword group obtaining means automatically detects the organs and pathologies represented by the second group of keywords from within the medical images, instead of those represented by the first group of keywords.

A configuration may be adopted, wherein:

the third keyword group obtaining means automatically detects the organs and pathologies represented by a portion of the first group of keywords from within the medical images, only in cases that the portion of the first group of keywords match those included in the second group of keywords.

In the medical image information display apparatus, the medical image information display method, and the medical image information display program of the present invention, the common keywords and indicia that represent organs or pathologies that correspond to the common keywords are correlated and displayed. Thereby, keywords that represent the organs or pathologies described in image observation reports are automatically correlated and displayed with the organs or pathologies detected within the medical images. Therefore, text that represents organs or pathologies within the image observation reports and the organs or pathologies within the medical images can be easily correlated without the burden of linking operations. Further, image observation can be performed efficiently, because referring to text that represents organs or pathologies within generated image observation reports and organs or pathologies within medical images is facilitated.

A configuration may be adopted, wherein: the link data generating means further correlates phrases that precede and follow the common keywords within the image observation reports to the link data in addition to the common keywords; and the link data display means displays the phrases that precede and follow the common keywords in addition to the common keywords. In this case, not only are the keywords that represent organs or pathologies displayed, but phrases that follow and precede the keywords are also displayed. Therefore, a greater amount of information described in the image observation reports can be assessed, and accurate image observation becomes possible.

A configuration may be adopted, wherein the third keyword group obtaining means designates keywords that represent the narrowest concept as the keywords corresponding to the organs and pathologies, in the case that the same organs and pathologies are detected based on a plurality of the keywords. In this case, keywords that correspond to the narrowest concept of organs and pathologies can be obtained. Therefore, more detailed information regarding the organs and pathologies can be obtained in the medical images.

A configuration may be adopted, wherein the second keyword group obtaining means designates phrases that represent the narrowest concept as the detected phrases, in the case that a plurality of phrases that represent the same organ are detected within the image observation reports. In this case, keywords that correspond to the narrowest concept of organs and pathologies can be obtained. Therefore, more detailed information regarding the organs and pathologies can be obtained in the medical images.

A configuration may be adopted, wherein the medical image information display apparatus of the present invention further comprises: image observation report display means, for displaying the image observation reports; and common keyword specifying means, for specifying the common keywords; wherein: the link data generating means links the common keywords displayed by the link data display means to the common keywords within the image observation reports by hyperlinks; and the image observation report display means displays the entirety of the image observation reports in response to specification of the common keywords displayed by the link data display means, with the specified common keywords being displayed in an emphasized manner compared to other text within the image observation reports. In this case, the specified common keywords can be easily discriminated, and image observation is facilitated.

A configuration may be adopted, wherein the medical image information display apparatus of the present invention further comprises: list display means, for displaying a common keyword list that includes a plurality of common keywords; wherein: the link data display means displays indicia that represent an organ or a pathology corresponding to a specified common keyword, in response to specification of the specified common keyword from among the plurality of common keywords displayed in the common keyword list. In this case, the organs or the pathologies corresponding to the common keywords can be easily referred to, and efficient image observation becomes possible.

A configuration may be adopted, wherein: the second keyword group obtaining means obtains the second group of keywords from a plurality of image observation reports regarding the same patient; and the link data generating means further correlates image observation report specifying data that specifies image observation reports that include the common keywords with the link data. In this case, the second keywords are detected from among a plurality of image observation reports. Therefore, more information can be detected than from a single image observation report, and accurate image observation becomes possible.

A configuration may be adopted, wherein: the link data generating means correlates the common keywords included in the newest image observation report from among the plurality of image observation reports and image observation report specifying data that specifies the newest image observation report with the link data, when phrases corresponding to the same common keywords are detected within the plurality of image observation reports. In this case, information described in the most recent image observation report can be detected, and therefore, accurate image observation becomes possible.

The link data generating means may generate an image observation report list that includes image observation report specifying data that specify a plurality of image observation reports when phrases corresponding to the same common keywords are detected within the plurality of image observation reports, and link the image observation report specifying data included in the image observation report list and the same common keywords included in the image observation reports corresponding to the image observation report specifying data by hyperlinks; and the list display means may further display the image observation report list. In this case, a plurality of image observation reports corresponding to the common keywords can be easily referred to, and therefore, efficient image observation becomes possible.

A configuration may be adopted, wherein: the third keyword group obtaining means automatically detects the organs and pathologies represented by the second group of keywords from within the medical images, instead of those represented by the first group of keywords. In this case, the need to automatically detect the organs or pathologies corresponding to all of the first group of keywords is obviated, and therefore, the organ detecting process or the pathology detecting process will become more efficient.

A configuration may be adopted, wherein: the third keyword group obtaining means automatically detects the organs and pathologies represented by a portion of the first group of keywords from within the medical images, only in cases that the portion of the first group of keywords match those included in the second group of keywords. In this case, the need to automatically detect the organs or pathologies corresponding to all of the first group of keywords is obviated, and therefore, the organ detecting process or the pathology detecting process will become more efficient.

BRIEF DESCRIPTION OF THE DRAWINGS

FIG. 10 is a diagram that illustrates an example of a common keyword list displayed by the second embodiment.

FIG. 15 is a flow chart that illustrates a medical image information display process performed by the fourth embodiment.

FIG. 16 is a functional block diagram that illustrates the medical image information display functions of a fifth embodiment.

DESCRIPTION OF THE PREFERRED EMBODIMENTS

Figure 1:
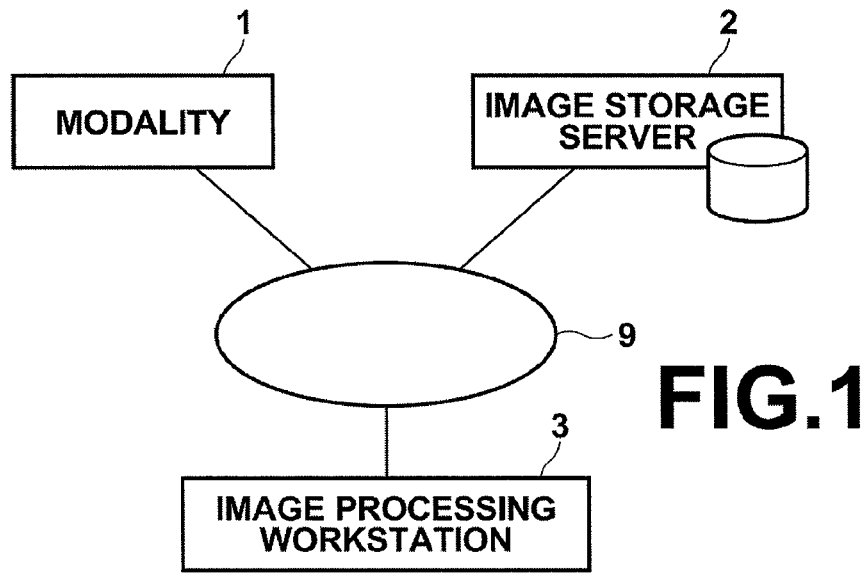
FIG. 1 is a schematic diagram that illustrates an image information display apparatus according to a first embodiment of the present invention.

FIG. 1 is a diagram that illustrates the hardware structure of a medical image information display apparatus according to a first embodiment of the present invention. As illustrated in FIG. 1, the system includes: a modality 1; an image storage server 2; and an image processing workstation 3. The modality 1, the image storage server 2, and the image processing workstation 3 are connected via a network 9 such that they can communicate with each other.

The modality 1 obtains medical images V that represent subjects. Specifically, the modality 1 is a CT apparatus, an MRI apparatus, a PET apparatus, an ultrasound apparatus, or the like.

The image storage server 2 is a computer that stores and manages the medical images V obtained by the modality 1 and medical images V which are generated by image processes at the image processing workstation 3. The image storage server 2 is equipped with a high capacity external storage device and database management software (for example, ORDB (Object Relational Database) management software).

The image processing workstation 3 is a computer that administers image processes onto medical images V obtained by the modality 1 and medical images V obtained from the image storage server 2 in response to requests by diagnosticians, and displays the processed images.

The storage format and communications among each component via the network 9 are based on a protocol, such as the DICOM (Digital Imaging and Communications in Medicine) protocol.

Next, the structures related to the medical image processing functions of the first embodiment of the present invention will be described.

Figure 2:
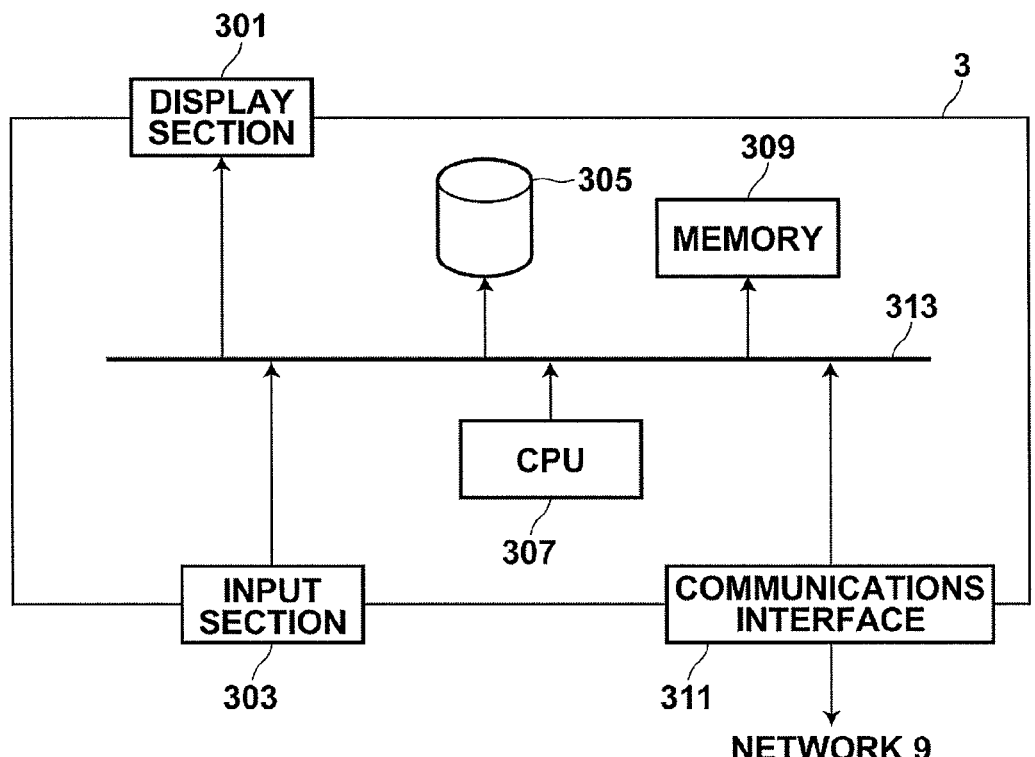
FIG. 2 is a block diagram that illustrates the structure of the first embodiment.

FIG. 2 is a schematic block diagram that illustrates the structure of the image processing workstation 3. As illustrated in FIG. 2, the medical image information display apparatus of the first embodiment is equipped with the image processing workstation 3, which includes: a display section 301 such as a liquid crystal monitor, for performing various types of display; an input section 303 constituted by a keyboard, a mouse, and the like, for performing various types of input; a hard disk 305, in which various programs, including a medical image information display program of the present invention and programs for controlling the image information display program of the present embodiment, as well as various types of data such as image data are stored; a CPU 307, for controlling the image information display device of the present embodiment by executing the various types of programs; a memory 309, which is utilized as a workspace during execution of programs; and a communications interface 311 that connects the image processing workstation 3 to the network 9 via a bus 313.

Note that in all of the embodiments to be described herein, the functions of the present invention are realized by a computer executing external programs installed therein. These programs may be installed from recording media such as CD-ROM's, flash memory and FD's. Alternatively, the programs may be installed after being supplied from an external recording medium via a network as a data group that includes the programs.

Figure 3:
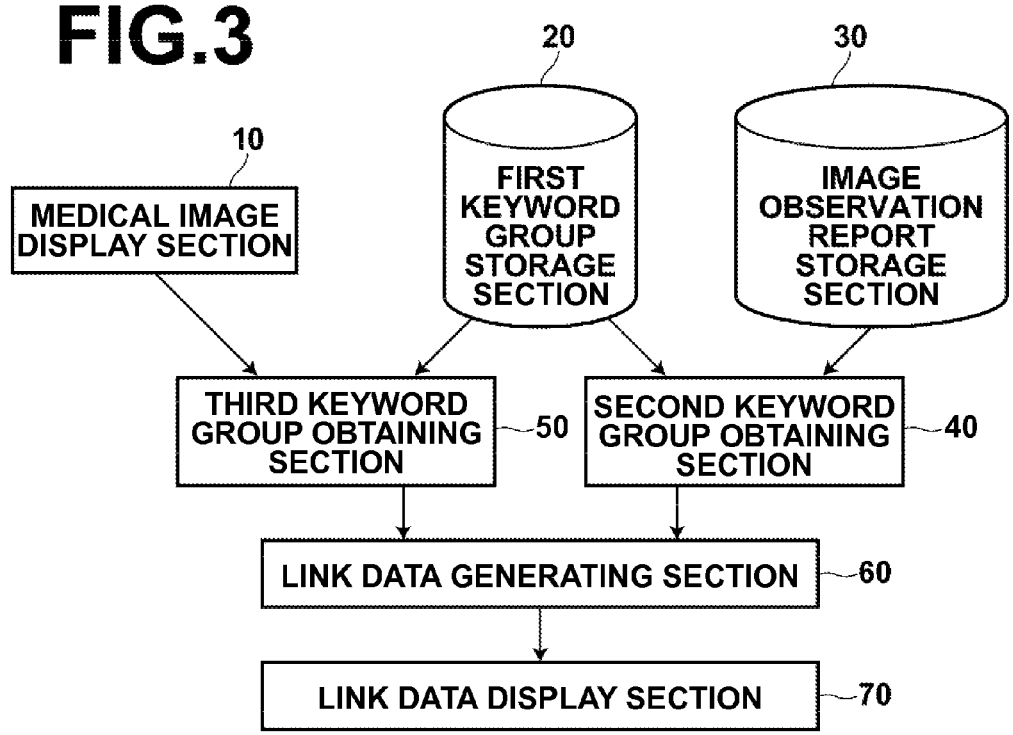
FIG. 3 is a functional block diagram that illustrates the medical image information display functions of the first embodiment.

FIG. 3 is a functional block diagram that illustrates components related to medical image information display functions of the first embodiment. As illustrated in FIG. 3, the medical image information display functions of the present invention are realized by: medical image display means 10, for obtaining medical images V via the network 9 in response to requests from the modality 1 or the image storage server 2 and for displaying the medical images V; image observation report storage means 30, for storing image observation reports related to the medical images V; first keyword group storage means 20, for storing a first group of keywords that include keywords that represent organs or pathologies (hereinafter, "organs or pathologies" will be referred to as "organs, etc."); second keyword group obtaining means 40, for detecting phrases that match the stored first group of keywords from within the image observation reports, and for obtaining a second group of keywords that include the detected phrases; third keyword group obtaining means 50, for automatically detecting the organs and pathologies represented by the stored first group of keywords from within the medical images V, and for obtaining a third group of keywords that include keywords corresponding to the detected organs, etc.; link data generating means 60, for comparing the second keyword group and the third keyword group, obtaining common keywords that match between the two groups, and for generating link data, in which each of the obtained common keywords are each correlated with the organs and pathologies that the common keywords correspond to; and link data display means 70, for displaying the common keywords, correlated with indicia that represent the organs and pathologies corresponding to the common keywords.

The medical image display means 10 includes the communications interface 311 that obtains the medical images V via the network 9 and the display section 301 for displaying the obtained medical images V. The medical image display means 10 causes the medical images V obtained via the network 9 to be displayed by the display section 301.

The first keyword group storage means 20 is mainly constituted by the hard disk 305, and is a database of organ names that includes groups of keywords that represent organs, etc. The groups of keywords that represent organs, etc. are registered in advance. Registration of the keywords that represent organs, etc. may be performed by input via the input section 303. Alternatively, keywords that represent organs, etc. may be prepared in advance, and copied via the network 9 or from recording media. In addition, keywords that represent pathologies may also be registered in the first keyword group storage means 20. Here, the keywords which are registered that represent organs include the names of organs, epithets associated with the organs, symbols that represent the organs, and abbreviations thereof. In addition, the "keywords that represent pathologies" include the names of diseases, epithets associated with the diseases, symbols that represent the diseases, and abbreviations thereof. Specifically, "lung", "liver", "bone", and "heart" may be employed as keywords that represent organs. Likewise, keywords that represent diseases or symptoms, such as "lung cancer", "liver cell carcinoma", "liver cysts", "hepatic hemangioma", "bleeding in the liver region", "bleeding in the brain region", "abnormal patterns", "calcifications", "abnormal blood vessels", and interstitial lung diseases such as "consolidation", "Ground Glass Opacity (GGO)", "Crazy Paving", "honeycomb patterns", "emphysema patterns", and "nodular patterns" may be employed as the keywords that represent pathologies.

The image observation report storage means 305 is mainly constituted by the hard disk 305, and stores image observation reports that include text that represents the contents of pathologies of diseased regions within the medical images V therein.

The second keyword group obtaining means 40 is mainly constituted by the CPU 307, and detects keywords from within the image observation reports recorded in the image observation report storage means 30 that match keywords of the first keyword group.

The third keyword group obtaining means 50 is mainly constituted by the CPU 307. The third keyword group obtaining means 50 performs CAD (Computer Aided Diagnosis) that employs computer processes to automatically detect candidates for organs, etc. represented by the keywords included in the first keyword group, to automatically detect the organs, etc. Then, the third keyword group obtaining means 50 determines a third keyword group including keywords that represent the automatically detected organs, etc. Known methods for automatically detecting organs, etc. from within medical images may be employed to automatically detect the organs, etc. Specific examples of methods for extracting organs include: the techniques disclosed in Japanese Unexamined Patent Publication Nos. 2001-137230 and 2008-253293 with respect to the lung field; the techniques disclosed in Japanese Unexamined Patent Publication No. 2001-283191 and U.S. Pat. No. 7,046,833 with respect to the liver; the technique disclosed in Japanese Unexamined Patent Publication No. 2008-043564 with respect to bones; and the technique disclosed in Japanese Unexamined Patent Publication No. 2004-141612 with respect to the heart.

In addition, the third keyword group obtaining means 50 may employ known methods to automatically detect pathologies. Examples of such known methods include: the techniques disclosed in U.S. Pat. No. 7,058,210, Japanese Unexamined Patent Publication No. 2003-271924 and in K. Kubota et al., "Evaluation of Computer-Aided Diagnosis system for Lung Cancer based on Helical CT images", Technical Report of the Institute of Electronics, Information and Communication Engineers, MI2001-41, pp. 41-46, 2001 with respect to lung cancer; the technique disclosed in S. Kido et al., "Intelligent CAD for diffuse lung diseases", Journal of 4th Symposium "Computer Aided Diagnosis of Multi Dimensional Medical Images", Specified Area Research Funded by the Ministry of Education, Culture, Sports, Science and Technology, pp. 45-54, 2007, with respect to detecting interstitial lung disease such as consolidation, Ground Glass Opacity (GOO), Crazy Paving, honeycomb patterns, emphysema patterns, and nodular patterns; Y. Wakida et al., "Liver Cancer Detection based on a Temporal Density Feature from Abdominal Dynamic X-ray CT Images", Journal of Computer Aided Diagnosis of Medical Images, Vol. 10, No. 1, pp. 1-10, 2007, with respect to hepatic cancer; and H. Fujita et al., "Intelligent Computer-aided Diagnosis Based on Normal Structure Recognition of Human Body", Journal of 4th Symposium "Computer Aided Diagnosis of Multi Dimensional Medical Images", Specified Area Research Funded by the Ministry of Education, Culture, Sports, Science and Technology, pp. 55-60, 2007, with respect to liver cell carcinoma, liver cysts, hepatic hemangioma, bleeding in the liver region, and bleeding in the brain region. Other examples of applicable known methods for detecting pathologies include: the technique disclosed in U.S. Pat. No. 7,546,154 with respect to abnormalities in the blood vessels; the technique disclosed in U.S. Pat. No. 5,940,527 with respect to abnormal pattern candidates; and the technique disclosed in Japanese Unexamined Patent Publication No. 8(1996)-215183 with respect to calcified regions. Any other methods that enable automatic detection of other organs and pathologies may be utilized.

In cases that organs, etc. are discovered by automatic detection, the positions of the organs, etc. and keywords that represents the organs, etc. are input to the link data generating means. In this case, the organs, etc. may be input as regions within the medical images V, or may be input as points that indicate representative positions of the regions of the organs, etc., such as the barycenters thereof. In cases that the medical images are constituted by a group of tomographic images, the organs, etc. may be automatically detected from within all of the tomographic images, or may be detected from within a portion of the tomographic images.

The keywords that represent the organs, etc. are keywords that match those included in the first keyword group. Alternatively, the keywords that represent the organs, etc. may be synonyms of the keywords included in the first keyword group.

The link data generating means 60 is mainly constituted by the CPU 307. The link data generating means 60 compares the second keyword group obtained by the second keyword group obtaining means 40 and the third keyword group obtained by the third keyword group obtaining means 50, obtains common keywords that match among the two, and generates link data, in which the common keywords are correlated with the organs or pathologies corresponding thereto, for each common keyword.

The link data display means 70 is mainly constituted by the display section 301. The link data display means 70 displays the common keywords and indicia that represent the organs or pathologies corresponding thereto in a correlated manner. The indicia that represent organs, etc. may be the outline of a region, such as indicia 135C illustrated in FIG. 5. Alternatively, other types of known indicia capable of indicating positions, such as point, crosses, and arrows may be employed. In addition, in the indicia that represent the organs, etc. indicate diseased regions as circles, rectangles, arrows, or closed surfaces, the indicia may be displayed as specified points within the diseased regions. The specified points may be the barycenters or the centers of the diseased regions, or points that represent the characteristics of the diseased regions. In addition, that the common keywords and the indicia are displayed in a correlated manner means that the common keywords and the indicia are enabled to be recognized as corresponding to each other. For example, the common keywords and the indicia that represent the organs, etc. may be connected by correlating indicia such as lines, arrows, or bubbles that emanate from the indicia that represent the organs, etc. Alternatively, the common keywords may be displayed in the vicinity of the indicia that represent the organs, etc. that they are correlated with. In addition, in cases that only one common keyword and one indicium that represents an organ, etc. are present, simply displaying the one common keyword and the one indicia is considered to be "displayed in a correlated manner", even if the correlating indicia are not displayed or the common keyword is not displayed in the vicinity of the indicium that represents the organ, etc.

The operations for inserting the common keywords into the image observation reports performed by the present embodiment will be described with reference to FIG. 4 and FIG. 5.

Figure 5:
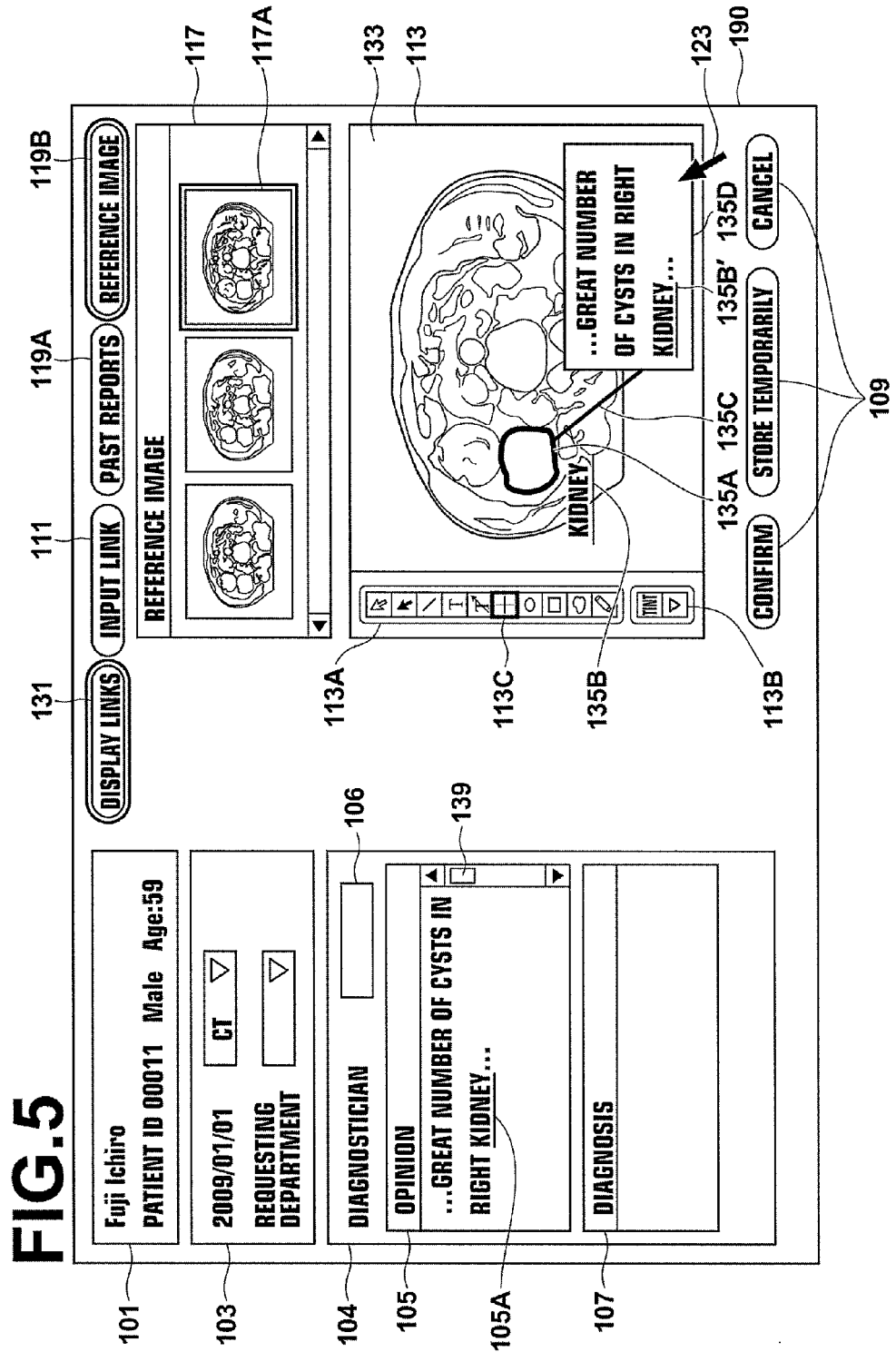
FIG. 5 is a diagram that illustrates an example of an image observation report and a medical image displayed by the medical image information display functions of the first embodiment.

FIG. 5 is a diagram that illustrates an example of link data and a medical image displayed by the medical image information display functions of the first embodiment. A medical image display screen 190 is illustrated in FIG. 5 as an example of a medical image information display screen.

First, the configuration of the medical image display screen 190 of FIG. 5 will be described. The medical image display screen 190 of FIG. 5 includes a patient data region 101, in which data regarding a patient are displayed. The name of the patient, a patient ID, the sex and the age of the patient, obtained from DICOM header data, for example, are displayed in the patient data region 101. The imaging date, the modality, and the department which requested imaging of a medical image V are input to a medical image data region 103, in which data regarding the medical image V are displayed, via the input section 303 such as a mouse or keyboard, or from DICOM header data. A diagnostician name field 106, an observation field 105, and a diagnosis field 107 are provided in an image observation report region 104. Input to and editing of the diagnostician name field 106, the observation field 105, and the diagnosis field 107 may be performed by physicians via the mouse and the keyboard. The observation field 105 and the diagnosis field 107 are displayed such that observations and diagnoses which have been generated previously can be referred to. In addition, in cases that the observation field 105 contains a large amount of descriptions of the image observation report, which cannot be displayed simultaneously within the observation field 105, referral to the entirety of the contents of the observations is enabled by moving a cursor 139.

Further, buttons necessary to access data, such as a past report selection button 119A, a reference image selection button 119B are provided in the medical image display screen 190, as well as a link input selection button 111, which enables link input in the present embodiment. The link input selection button 111 may be of any known configuration, within the range of achieving the purpose thereof.

If the past report selection button 119A is selected, past reports are displayed in a selectable manner within a reference data region 117. If the reference image selection button 119B is selected, thumbnail images of medical images V are displayed in the reference data region 117, as illustrated in FIG. 5. That is, the reference data region 117 displays reference data, such as past reports and thumbnail images of medical images V.

The medical image display screen 190 also includes a detailed image display region 113. In the example illustrated in FIG. 5, a thumbnail image 117A is selected from among a plurality of thumbnail images of medical images within the reference data region 117, and a medical image 133 corresponding to the thumbnail image 117A is displayed in the detailed image display region 113.

Editing buttons 113A, 113B, and 113C for processing and editing medical images displayed in the detailed image display region 113 are provided in the detailed image display region 113. In addition, a "Display Link" button 131, for turning display of link data obtained by the present embodiment ON/OFF, is also included in the medical image display screen 190. In the case that display of the link data is turned ON, link data generated by the present invention are displayed. In the case that display of the link data is turned OFF, the link data are not displayed.

Next, the process by which the first embodiment displays link data will be described with reference to FIG. 4. FIG. 4 is a flow chart that illustrates the steps of an operation performed by the medical image information display apparatus of the first embodiment.

First, keywords that match keywords stored in the first keyword group storage means 20 are detected form within an image observation report (step ST101). At this time, an "Input Link" button 111 included in the medical image display screen 190 of FIG. 5 may be selected by the input section 303 to initiate obtainment of link data. In the case that such keywords are detected (YES in step ST102), the detected keywords are obtained as a second keyword group. In the case that such keywords are not detected (NO in step ST102), the link data display process ends.

It is preferable for the second keyword group obtaining means 40 to store keywords included in the first keyword group and synonyms corresponding thereto, to search the text within the image observation report for the keywords included in the first keyword group and synonyms thereof, and to designate keywords and synonyms thereof detected in the image observation report as keywords to be included in the second keyword group. In this case, keywords that represents organs, etc. and synonyms thereof can be searched for within the image observation report, and therefore, information that represents organs, etc. being overlooked can be suppressed.

Next, the organs, etc. represented by the keywords stored in the first keyword group storage means 20 are detected from within a medical image using an automatic detecting technique (step ST103).

If organs, etc. are detected, data that specify the medical image 133 that the detected organs, etc. are pictured in, and organ data that represent the organs, etc. such as the coordinates of the organs, etc., are obtained by the third keyword obtaining means 50. The data that specify the medical image 133 that the detected organs, etc. are pictured in may be a number which is a combination of a series number and a slice number, in the case that the medical image 133 is a part of a series of tomographic images. Further, the data that specify the medical image 133 may be data regarding an image ID, obtained from DICOM header data. In cases that the organs, etc. are detected as points, positional data may be obtained as coordinate values within the medical image 133. In cases that the organs, etc. are detected as lines or regions, the ends of the lines within the medical image 133 or functions that represent the regions may be obtained as the organ data.

In the case that organs, etc. are not detected (NO at step ST104), the link data display process ends. In the present embodiment, the keywords are searched for in the image observation report, and then the organs, etc. are detected within the medical image. However, the present invention is not limited to a configuration in which the detection processes are performed in this order. The organs, etc. may be detected within the medical image first, and then the keywords may be searched for in the image observation report. Alternatively, the search for keywords within the image observation report and the detection of organs, etc. within the medical image may be performed simultaneously.

In the case that organs, etc. are detected (YES in step ST104), keywords that represent the detected organs, etc. are obtained as a third keyword group. The keywords of the second keyword group and the keywords of the third keyword group are compared. In the case that there are no matching keywords between the second keyword group and the third keyword group (NO in step ST105), the link data display process ends.

In the case that keywords that match between the second keyword group and the third keyword group are present (YES in step ST105), the link data generating means 60 obtains the matching keywords as common keywords (step ST106). That is, the common keywords are keywords which are described within the image observation report, and that represent organs, etc., detected from within the medical image. The link data generating means 60 generates link data that include the common keywords and the organs, etc. detected within the medical image.

Specifically, the link data include: (1) the name of the common keyword; (2) data that specify the medical image in which the organs, etc. were detected; and (3) the position of the organs, etc. The data that specify the medical image in which the detected organs, etc. are pictured in may be a number which is a combination of a series number and a slice number, in the case that the medical image in which a pathology is pictured is a part of a series of tomographic images. Examples of data that indicate the position of the organs, etc. include: coordinate values that represent the regions or outlines of the organs, etc.; and coordinate values of specific points within the regions of the organs, etc. The specific points may be the barycenters or the centers of the regions. Note that there are cases in which a keyword corresponding to a single common keyword is described at a plurality of locations within an image observation report, and cases in which organs, etc. corresponding to keywords are detected at a plurality of positions within medical images. In these cases, the plurality of locations at which the keyword corresponding to the common keyword is described in the image observation report, and the plurality of positions at which the plurality of organs, etc. are detected within the medical image, and data that specify the medical images that include the plurality of organs, etc. are included in the link data.

Next, the link data display means 70 obtains the link data from the link data generating means 60, and displays an indicium 135A that indicates the position of an organ, etc. and a common keyword 135B in a correlated manner on the medical image 133 (step ST107).

In the example of FIG. 5, the keyword "kidney" included in the first keyword group is detected as a keyword 105A within the image observation report, a region 135A that represents a "kidney" is detected within the medical image 133, link data that correlates the common keyword "kidney" with the region 135B that represents the "kidney" is generated, and the common keyword "kidney" (135B) is displayed along with the region 135A that represents the "kidney" on the medical image 133.

In the example of FIG. 5, that the common keyword 135B and the indicium 135A are correlated can be recognized by the two being displayed close to each other. In addition, a common keyword 135B' and phrases that precede and follow the common keyword 135B' in the image observation report may be displayed, as in the portion denoted by reference numeral 135D of FIG. 5 (hereinafter, "a common keyword and phrases that precede and follow the common keyword" will simply be referred to as "a comment that includes a common keyword"). Further, the common keyword 135B' or the comment that includes the common keyword 135B' may be correlated with the indicium 135A that represents the position of the organ, etc., by displaying a correlating indicia 135C. Note that in the description, the common keyword 135B and the common keyword 135B' are denoted by different reference numerals. However, the two are the same common keyword.

The common keyword 135B', the indicium 135A that represents the position of the organ, etc., and the comment 135D that includes the common keyword 135B' are displayed in the example of FIG. 5. An alternate configuration, in which the indicium 135A that represents the position of the organ, etc., and only one of the common keyword 135B' and the comment 135D that includes the common keyword 135B' are displayed, may be adopted. In this case, a correlating indicia 135C that correlates the indicium 135A that represents the position of the organ, etc, and one of the common keyword 135B' and the comment 135D that includes the common keyword 135B' may also be displayed.

Here, it is desirable for the outline of the detected organ, etc. to be displayed as the indicium that represents the organ, etc. However, the detected organs, etc. may be indicated by a different type of indicia that facilitates discrimination thereof. Examples of such different types of indicia include: coloration of the detected organs, etc.; figures such as circles that surround the organs, etc.; and points or figures such as rectangles displayed at a portion of the displayed organs, etc. In the case that the outline of the detected organ, etc. is displayed, the organ, etc. can be clearly recognized, and accurate image observation becomes possible.

In the case that a plurality of organs, etc. are detected from within a plurality of tomographic medical images, and only a portion of the detected organs, etc. is pictured within a displayed tomographic image 133, link data correlated to only the displayed organs, etc. are displayed. For example, in the case that a liver, a kidney, and a spleen are detected within a plurality of tomographic medical images, and only the kidney is pictured within a displayed medical image 113, only the indicium 135A that represents the kidney and the common keyword 135B corresponding thereto are displayed, from among the link data.

In the case that a keyword corresponding to a single common keyword 135B' is described at a plurality of locations within an image observation report, and the organ, etc. corresponding to the common keyword 135B' is detected at one position within a medical image, comments corresponding to each of the plurality of locations within the image observation report that the keyword corresponding to the single common keyword 135B may be generated. Then, all of the generated comments may be displayed in a manner correlated to the organ, etc. corresponding to the common keyword. Alternatively, only the common keyword 135B' may be displayed.

In the case that organs, etc. corresponding to a single common keyword 135B' are detected at a plurality of positions within medical images, and a keyword corresponding to the common keyword 135B' is detected at a single location within an image observation report, indicia that represent each of the plurality of organs, etc. corresponding to the common keyword 135B' may be displayed simultaneously. Then, the common keyword 135B' or comments including the common keyword 135B' may be displayed in a manner correlated with each of the indicia that represent the organs, etc.

In the case that organs, etc. corresponding to a single common keyword 135B' are detected at a plurality of positions within medical images, and a keyword corresponding to the single common keyword 135B' is described at a plurality of locations within an image observation report, indicia that represent each of the plurality of organs, etc. corresponding to the common keyword 135B' may be displayed simultaneously. Then, the common keyword 135B' may be displayed in a manner correlated with each of the indicia that represent the organs, etc. Alternatively, comments may be generated corresponding to each of the plurality of locations within the image observation report that the keyword corresponding to the single common keyword 135B is described. Then, all of the generated comments may be displayed in a manner correlated to the indicia that represent the organs, etc. corresponding to the common keyword 135B'.

The medical image information display apparatus of the first embodiment automatically detects common keywords within the image observation report and the organs, etc. corresponding to the common keywords. Then, the common keywords and the organs are correlated and displayed. Therefore, linking can be performed easily without the burden of linking operations. The keywords representing organs or pathologies within the image observation reports and the organs or pathologies within the medical images can be visually confirmed in a correlated manner, and accurate image observation is enabled. Because no operation is required to correlate the keywords that describe organs or pathologies within the image observation report and the corresponding organs, etc., the burden of correlating the positions of the organs, etc. with the image observation report is eliminated.

In the case that phrases that precede and follow the common keywords are displayed in addition to the common keywords, more detailed information regarding the organs, etc. can be obtained from the medical image, which facilitates image observation. There is a high probability that phrases that precede and follow text that represents organs, etc. in the image observation report describe the organs, etc. Therefore, it is considered that there is a high probability that information that aids in understanding of the organs, etc. will be displayed, if the phrases that precede and follow the keyword within the image observation report that correspond to the common keyword are displayed.

In the case that the correlating indicia are also displayed on the medical image, the correspondent relationships among the indicia that represent the organs, etc. and the common keywords or the comments including the common keywords will become clear. Therefore, more accurate image observation becomes possible.

It is preferable for the second keyword group obtaining means to designate phrases that represent the narrowest concept as the detected keyword, in the case that a plurality of phrases that match keywords within the first keyword group are detected within the image observation reports. For example, if the phrase "right upper lobe S1" is detected within an image observation report, from among the keywords "lungs", "right lung", "right upper lobe", and "right upper lobe S1", the phrase "right upper lobe S1" is detected as the keyword. In cases that keywords that represent narrower concepts are detected as keywords within the second keyword group, specific assessment of the organs, etc. becomes possible, and accurate image observation is enabled.

It is preferable for the third keyword group obtaining means to designate keywords that represent the narrowest concept as the detected keyword, in the case that a plurality of organs, etc. that match keywords within the first keyword group are detected within the medical images. For example, if the "right upper lobe S1" is detected within a medical image, from among the organs represented by the keywords "lungs", "right lung", "right upper lobe", and "right upper lobe S1", the "right upper lobe S1" is detected as the keyword. In cases that keywords that represent narrower concepts are detected as keywords within the third keyword group, specific assessment of the organs, etc. becomes possible, and accurate image observation is enabled.

Figure 6:
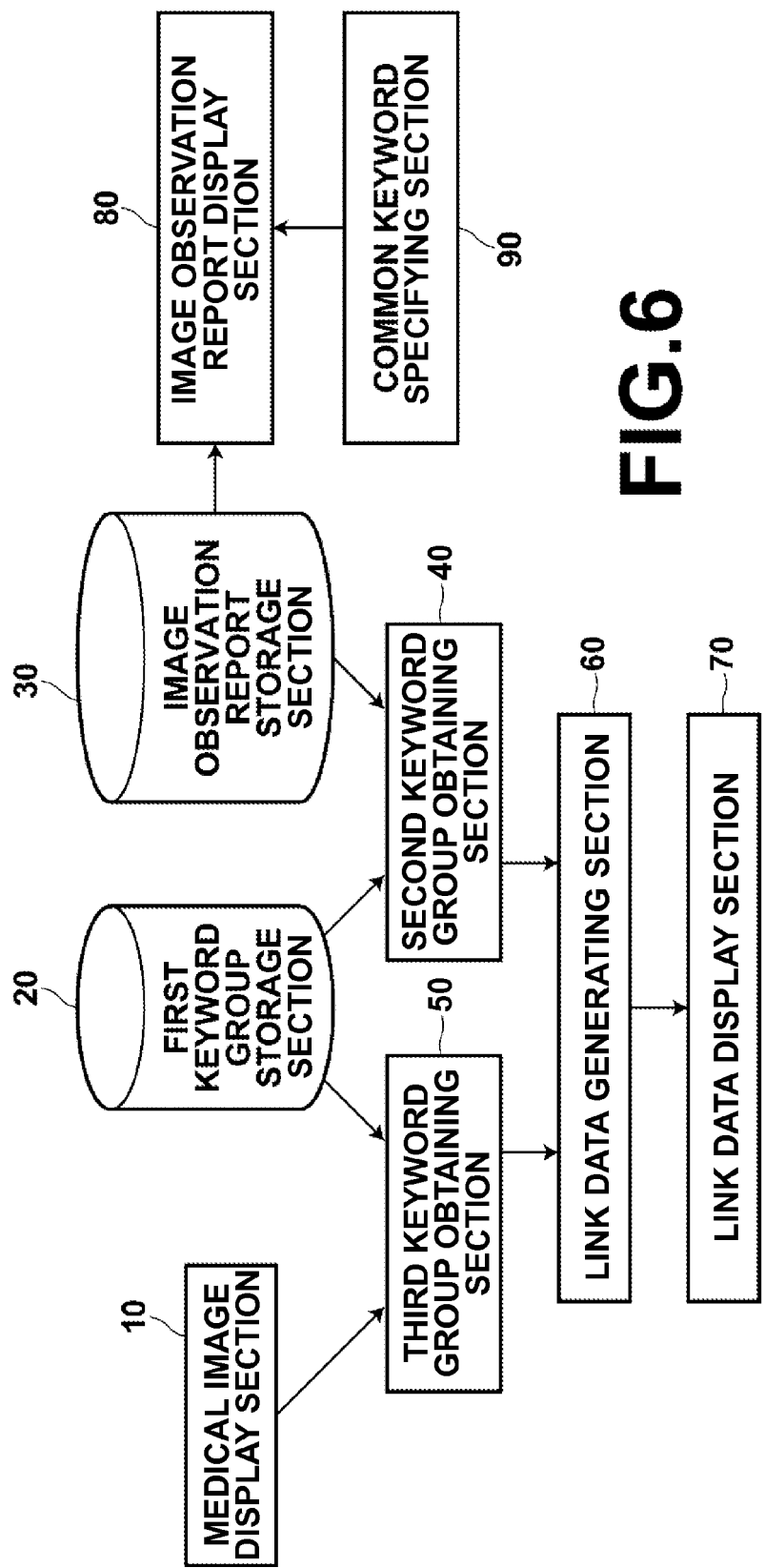
FIG. 6 is a functional block diagram that illustrates the medical image information display functions of a modified first embodiment.

A modification of the first embodiment will be described with reference to FIG. 5, FIG. 6, and FIG. 7. In the modification of the first embodiment, the link data display means 70 displays a keyword 105B described within an image observation report that corresponds to a common keyword 137B', linked to the common keyword 137B' by a hyperlink. FIG. 6 is a functional block diagram that illustrates the medical image information display functions of the modified first embodiment. The elements which are denoted by the same reference numerals as those illustrated in FIG. 3 are of the same configurations, and therefore, detailed descriptions thereof will be omitted.

An image observation report display means 80 is mainly constituted by the display section 301, and displays image observation reports stored in the image observation report storage means 30 in response to specifications by a common keyword specifying means 90.

The common keyword specifying means 90 is mainly constituted by the input section 303 for inputting diseased regions. The common keyword specifying means inputs a specified common keyword to the image observation report display means 80 in response to input or specification of the common keyword by an operator via the input section 303.

In FIG. 5, a selection tool 123 of the common keyword specifying means is specifying the common keyword 135B'. In response to this specification, the image observation report display means 80 displays the keyword 105A and the entirety of the image observation report that includes the keyword 105A in the observation field 105. The portion of the image observation report in the vicinity of the keyword 105A is displayed in the observation field 105, and the entirety of the image observation report may be referred to by scrolling the cursor 139, for example. Here, the manner in which the image observation report is displayed is not limited to that described above. The image observation report may be displayed in a separate window, or the entire image observation report may be displayed, in response to specification of the common keyword 135B'.

In addition, it is desirable for the specified common keyword 105A to be displayed in an emphasized manner compared to other text within the image observation report, in response to the specification of the common keyword 135B' by the common keyword specifying means 90. In FIG. 5, the keyword 105A is emphasized by being underlined and by being displayed in a bold font. However, the manner in which common keywords are emphasized is not limited to the example of FIG. 5. The specified common keywords may be displayed such that they are distinguishable from non specified text, by known techniques such as coloring the specified common keywords, coloring the backgrounds of the specified common keywords, underlining the specified common keywords, causing the specified common keywords to blink, displaying the specified common keywords in bold type, changing the font of the specified common keywords, changing the size of the font of the specified common keywords, and providing frames around the specified common keywords.

Note that in the case that a keyword corresponding to a single common keyword 135B' is described at a plurality of locations within an image observation report, the image observation report may be displayed such that the entirety thereof can be referred to, with the first instance that the corresponding keyword appears within the image observation report being displayed such that it is distinguishable from other text, in response to specification of the common keyword 135B'. Alternatively, comments that include the keyword that corresponds to the common keyword 135B' may be extracted from each location that the keyword is described at, and the comments may be displayed as a list from among which selection is possible. In this case, the image observation report may be displayed such that the entirety thereof can be referred to, with a selected comment that includes the common keyword being displayed such that it is distinguishable from other text, in response to specification of a common keyword within the comments that include the common keywords.

Alternatively, if a keyword corresponding to a single common keyword 135B' is described at a plurality of locations within an image observation report, the keywords may be correlated with indicia that represent corresponding organs, etc. In this case, comments corresponding to each of the plurality of locations at which the keyword is described within the image observation report may be generated. Then, the plurality of generated comments may be respectively correlated to all of the indicia that represent the organs, etc. corresponding to the common keyword 135B'. The image observation report may be displayed such that the entirety thereof can be referred to, with a keyword within a selected comment being displayed such that it is distinguishable from other text, in response to specification of a common keyword within the comments that include the common keywords.

In this modification of the first embodiment, the keywords 105A within the image observation report that correspond to the common keyword 135B' are linked to the common keyword 135B' by hyperlinks. Therefore, detailed information corresponding to the common keyword 135B' within the image observation report can be easily referred to, simply by specifying the common keyword 135B' within the image. Accordingly, efficient image observation becomes possible.

Figure 7:
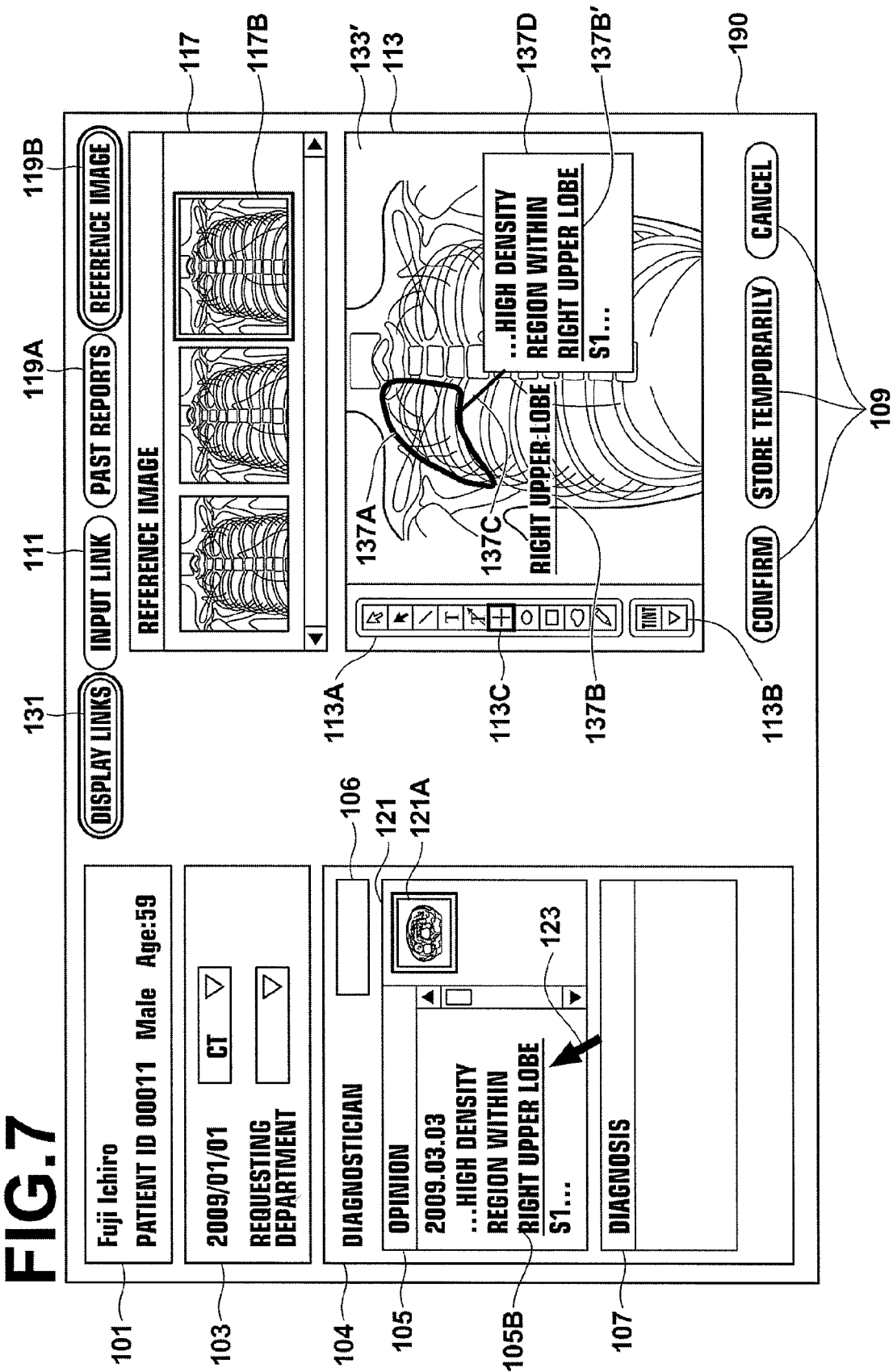
FIG. 7 is a diagram that illustrates an example of an image observation report and a medical image displayed by the medical image information display functions of another modification of the first embodiment.

FIG. 7 is a diagram that illustrates an example of an image observation report and a medical image displayed by the medical image information display functions of a second modification of the first embodiment. In the second modification of the first embodiment, the medical image display means 10 does not display the medical image 133 that includes the organs, etc. detected by the third keyword group obtaining means 50. Instead, the medical image display means 10 displays a reconstructed medical image 133' that includes the medical image 133, in which the detected organs, etc. are pictured. In addition, the link data display means 70 displays the link data within the reconstructed medical image 133'. Elements within FIG. 7 which are denoted by the same reference numerals as those illustrated in FIG. 5 are of the same configurations, and therefore, detailed descriptions thereof will be omitted.

First, a link position storage means obtains positions of pathologies within a slice image 115 and corresponding pathology text from a pathology storage means. Then, the coordinates of the positions of the pathologies within a medical image 133, which is reconstructed by stacking a plurality of slice images including the slice image 115, are calculated. Representative examples of reconstructed medical images are those which are reconstructed by the Ray Summation method, the MIP (Maximum Intensity Projection) method, and the MPR (Multi Planar Reconstruction) method.

The third keyword group obtaining means 50 detects organs, etc. represented by first keywords from within each tomographic image. When three dimensional medical images are reconstructed, surfaces that connect the outlines of the detected organs, etc. are generated, and the organs, etc. are obtained within the reconstructed three dimensional medical images. In addition, in the case that the reconstructed image is a projection image, the coordinates that represent the outlines of the organs, etc. within the reconstructed three dimensional medical image are projected onto the projection image, to obtain the organs, etc.

The three dimensional image is reconstructed from a great number of slice images, that is, a great number of two dimensional images which are sliced at predetermined thicknesses. Therefore, the coordinates of a point, which is specified on any one of the two dimensional images, within the three dimensional image can be calculated from the coordinates of the point and the position of the slice, and the coordinate position within the three dimensional image corresponding to the positions of pathology within the slice images can be specified. Accordingly, it is possible to indicate the positions of pathologies, which are specified within the slice images, within the three dimensional image.

It is desirable for outlines of the organs, etc. to be displayed as the indicia that represent the organs, etc. within the reconstructed medical image 133'. In the case that the outline of the detected organ, etc. is displayed, the organ, etc. can be clearly recognized, and accurate image observation becomes possible.

In FIG. 7, an indicium 137A that represents an organ, etc.; common keywords 137B and 137B'; a comment 137D that includes the common keyword; and a correlating indicia 137C are displayed as link data.

By displaying the indicium 137A that represents the organs, etc. within the reconstructed medical image, the position of a diseased region pictured in a slice image can be understood in another medical image. Therefore, the position of the diseased region can be more accurately understood. In addition, in the case that the indicium 137A that represents the organs, etc. is displayed within the reconstructed medical image 133', the position of the pathology can be understood three dimensionally, and more accurate image observation becomes possible with respect to the diseased reason. Further, if the reconstructed three dimensional medical image 133' is that which can be rotated, enlarged, or reduced and referred to, the indicium that represents the organs, etc. and the common keyword may be displayed in a manner coordinated with such rotation, enlargement, or reduction. In this case, the position of pathology can be understood from different angles and at different sizes, enabling more accurate image observation.

Further, in the case that the link data include a plurality of common keywords, all of the indicia that represent organs, etc. may be displayed within the reconstructed medical image. In this case, the organs, etc. that correspond to keywords described in the image observation report can be simultaneously displayed to a diagnostician. Therefore, a general indication of the amount of data regarding the organs, etc. described within the image observation report can be obtained, and generation of an image observation report can be aided more easily.

In addition, the medical image display means 10 may selectively display or not display individual organs, etc. within medical images reconstructed by the volume rendering method. It is desirable for the link data related to the organs, etc. to be displayed or not displayed in a manner coordinated with the displayed and non displayed organs, etc. In this case, information regarding the organs, etc. described in the image observation report can be referred to in units of individual organs, etc. Therefore, efficient diagnosis is enabled. In addition, the detected organs, etc. may be displayed with different colors so as to be distinguishable.

Further, in the second modification of the first embodiment, it is desirable for a keyword 105B within the image observation report corresponding to the common keyword 137B' to be linked to a medical image 121 that includes a detected organ, etc. by a hyperlink. In this case, the link data generating means 60 links the keyword 105B within the image observation report and a slice image 121A that includes the detected organ, etc. with a hyperlink when the common keyword 137B' is detected.

Then, the medical image display means 10 displays a thumbnail image of the slice image 121A that includes the organ, etc. detected by the third keyword group obtaining means 40 in an attached image display region 121 in response to the selection tool 123 of the common keyword specifying means 90 specifying the keyword 105B within the image observation report. In addition, an indicium (not shown) that indicates the position of a pathology is displayed within the slice image 121A by the link data display means 70, in response to specification of the keyword 105B. Here, the manner in which the medical image that includes the diseased reason is not limited to that described above. The slice image 121A may be displayed in a separate window in response to specification of the keyword 105B. As a further alternative, the slice image 121A may be displayed as a detailed medical image and not as a thumbnail image. Note that in the case that there are a plurality of organs, etc. that correspond to a single common keyword that corresponds to the keyword 1056B, all of the plurality of images that the organs, etc. are pictured in may be displayed.

In the second modification of the first embodiment, the keyword 105B within the image observation report that correspond to the common keyword 137B' are linked to the medical image 121A that includes the detected organs, etc. by hyperlinks. Therefore, the slice image 121A corresponding to the keyword 105B within the image observation report can be easily referred to, simply by specifying the common keyword 105B within the image. Accordingly, efficient image observation becomes possible. According to the second modification of the first embodiment, the keyword 105B within the image observation report that corresponds to the common keyword 137B' within the reconstructed medical image 133' is referred to, and the slice image 121A corresponding to the keyword 105B can be referred to. Therefore, obtainment of detailed corresponding information is greatly facilitated, and efficient image observation is enabled.

In addition, linking operations to link the keyword 105B within the image observation report to the medical image 121A that includes the detected organs, etc. are performed without operator intervention. Therefore, generation of image observation reports in which the organs, etc. pictured in medical images are linked to keywords that represent the organs, etc. is facilitated.

Figure 8:
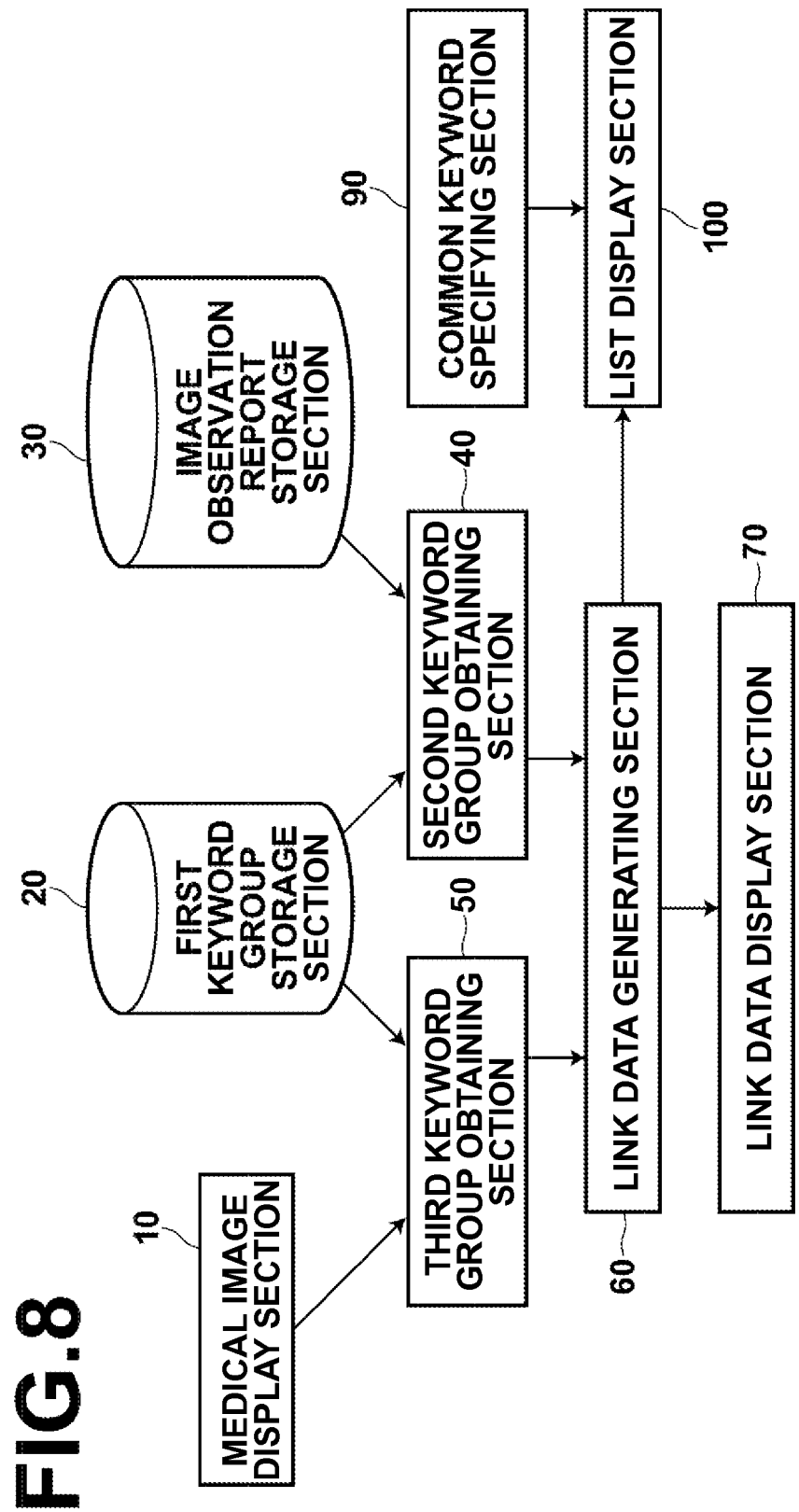
FIG. 8 is a functional block diagram that illustrates the medical image information display functions of a second embodiment.

A second embodiment of the present invention will be described with reference to FIGS. 8, 9, and 10.

In the second embodiment, a common keyword list that includes a plurality of detected common keywords is generated and displayed. FIG. 8 is a functional block diagram that illustrates the medical image information display functions of the second embodiment. The elements illustrated in FIG. 8 are the same as those illustrated in FIG. 3, except for a common keyword specifying means 90 and a list display means 100. The common keyword specifying means 90 is the same as that illustrated in FIG. 6. Accordingly, detailed descriptions of elements which are the same as those described previously will be omitted.

The list display means 100 is mainly constituted by the display section. The list display means 100 obtains a common keyword list from the link data generating means 60 and causes the common keyword list to be displayed by the display section.

Figure 9:
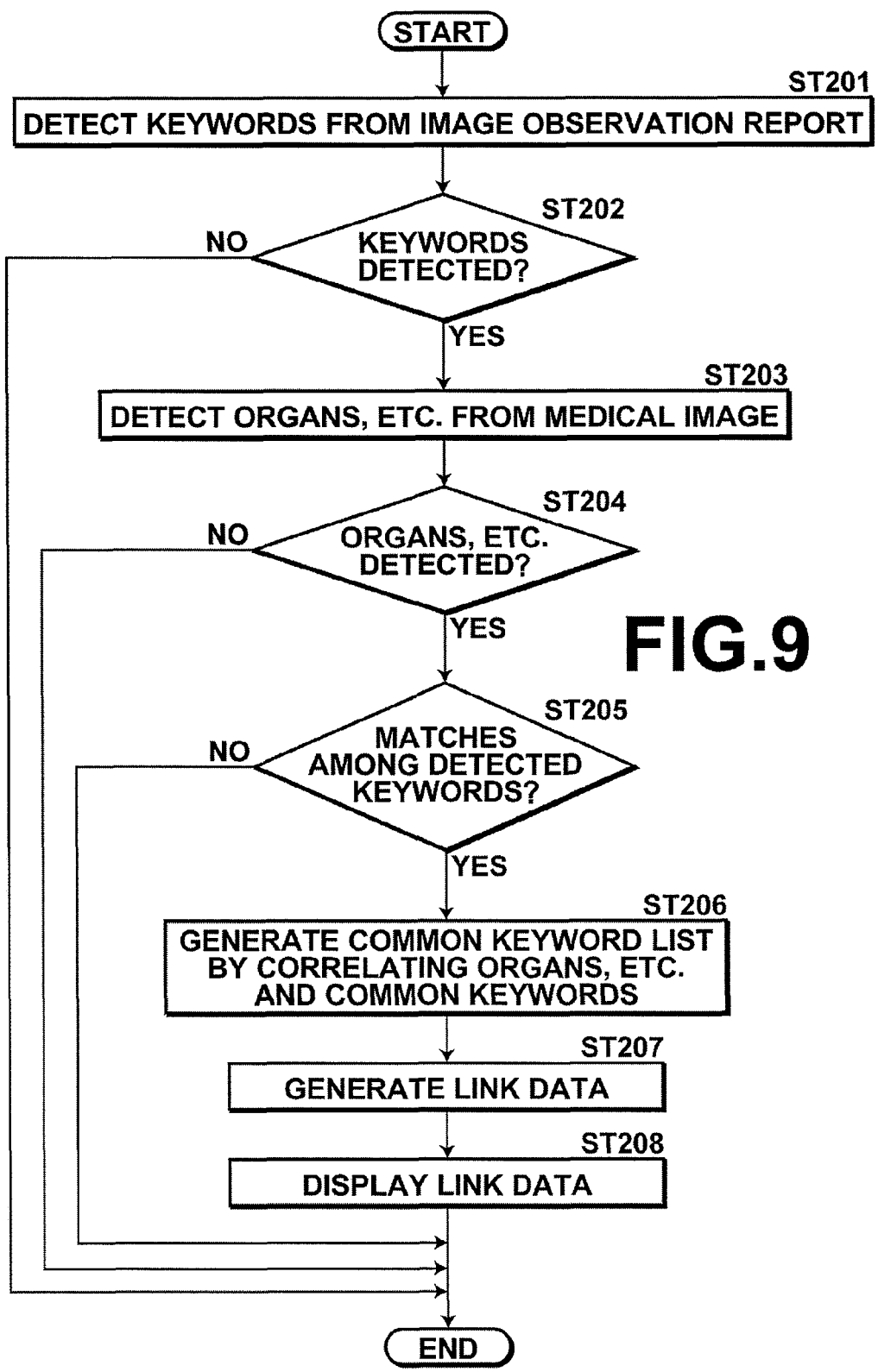
FIG. 9 is a flow chart that illustrates a medical image information display process performed by the second embodiment.

FIG. 9 is a flow chart that illustrates a medical image information display process performed by the second embodiment. Steps ST201 through ST205 are the same as steps ST101 through ST105. Therefore only step ST206 and the steps following thereafter which differ from those illustrated in FIG. 4 will be described.

The link data generating means 60 generates a common keyword list 150 that includes a plurality of detected common keywords (step ST206). As illustrated in FIG. 10, the common keyword list 150 is a list in which common keywords 150A and 150B are correlated with phrases within an image observation report that correspond to the common keywords 150A and 150B. It is desirable for the phrases within the image observation report that correspond to the common keywords to be phrases that include the keywords corresponding to the common keywords and phrases that follow the keywords within the image observation report. Alternatively, the phrases within the image observation report that correspond to the common keywords may be phrases that include the keywords and phrases that precede and follow the keywords within the image observation report. Note that there may be cases in which a keyword corresponding to a single common keyword 150A is described at a plurality of locations within an image observation report, and cases in which a plurality of organs, etc. corresponding to a single common keyword 150A are detected within a medical image. In these cases, information regarding the number of times and the locations at which the keyword corresponding to the single common keyword 150A is described in the image observation report, and information regarding the number of organs, etc. corresponding to the single common keyword 150A may also be displayed within the list.

Figure 4:
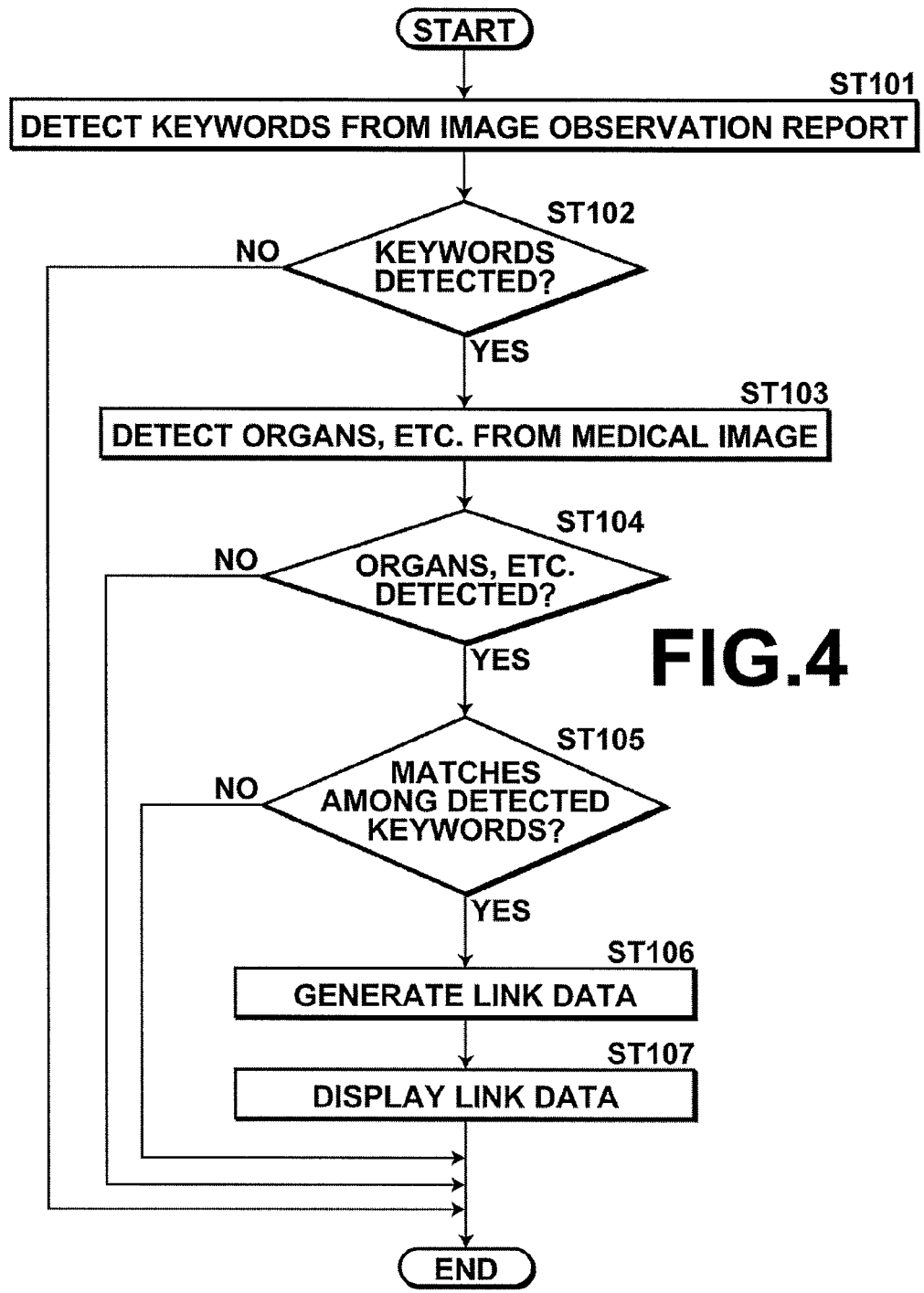
FIG. 4 is a flow chart that illustrates a medical image information display process performed by the first embodiment.

The link data generating means 60 adds the common keyword list to the link data generated in step ST106 of FIG. 4. The link data display means 70 displays only the common keyword list from among the link data. Comments that include a specified common keyword and indicia that represent organs corresponding to the specified common keyword are displayed in a correlated manner, in response to specification of the common keyword within the common keyword list 150 by the common keyword specifying means 90. Specifically, if the common keyword 150A listed in the common keyword list 150 of FIG. 10 is specified, link data, such as the indicium 137A that represents the organs, etc. of FIG. 7, the comment 137D that includes the common keyword 137b', and the correlating indicial 317C are displayed (step ST208). Note that in the case that a plurality of organs, etc. that correspond to a single common keyword 150A are detected within a medical image, all of the indicia that represent the organs, etc. may be displayed. In the case that a keyword corresponding to the single common keyword 135B' is described at a plurality of locations within an image observation report, comments may be generated corresponding to each of the plurality of locations within the image observation report that the keyword corresponding to the single common keyword 150A is described. Then, all of the generated comments may be displayed in a manner correlated to the indicia that represent the organs, etc. corresponding to the common keyword 150A'.

In the case that the common keyword list that includes the plurality of detected common keywords is generated and displayed, the common keywords can be assessed as a catalog. In addition, the organs, etc. described in the image observation report can be easily discriminated and displayed. Thereby, efficient diagnosis is enabled.

Indicia that represent the organs, etc. corresponding to the common keyword 150A may be displayed within the tomographic image 133 in response to specification of the common keyword 150A within the common keyword list 150, as in the first embodiment. In addition, indicia that represent the organs, etc. corresponding to the common keyword 150A may be displayed within the reconstructed medical image 133' in response to specification of the common keyword 150A within the common keyword list 150, as in the second modification of the first embodiment. In the case that the indicia that represent the organs, etc. corresponding to the common keyword 150A are displayed in the tomographic image 133, the medical image display means 10 may display a tomographic image in which the detected organ, etc. is pictured with the largest area, in response to specification of the common keyword 150A. For example, in the case that the organs, etc. are pathologies, the tomographic image in which the area of the pathology is greatest is displayed. Therefore, the need for a physician to search for a tomographic image in which the area of the pathology is greatest is obviated, and efficient diagnosis becomes possible.

Figure 11:
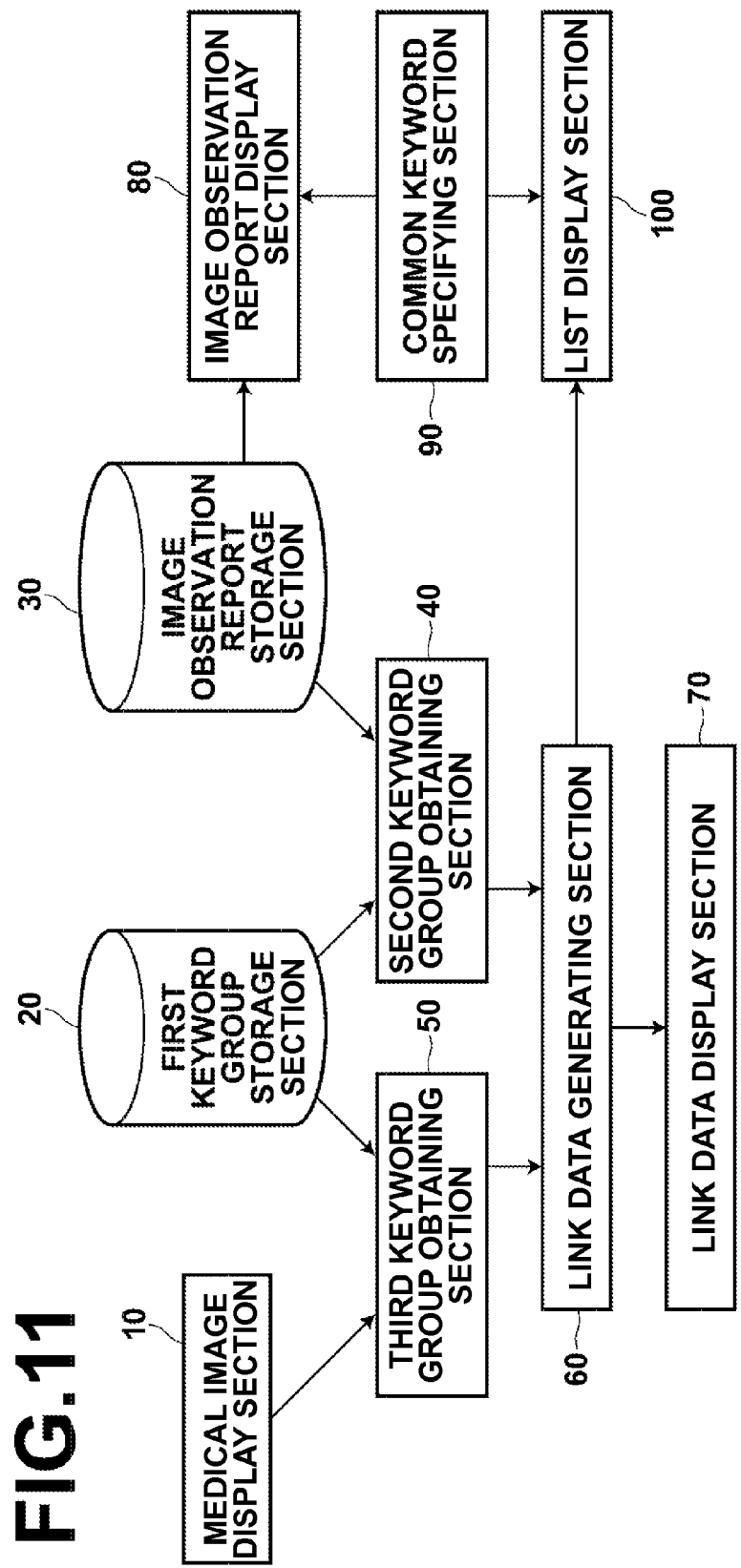
FIG. 11 is a functional block diagram that illustrates the medical image information display functions of a third embodiment.

A third embodiment of the present invention will be described with reference to FIGS. 11, 12, and 13.

In the third embodiment, a image observation report list that includes data that specify a plurality of image observation reports that include a single common keyword is generated and displayed. FIG. 11 is a functional block diagram that illustrates the medical image information display functions of the third embodiment. The third embodiment is the same as the embodiment illustrated in FIG. 3, except that an image observation report display means 80, a common keyword specifying means 90, and a list display means 100 are provided. The common keyword specifying means 90 is the same as that illustrated in FIG. 6. Accordingly, detailed descriptions of elements which are the same as those described previously will be omitted. However, the image observation report storage means 30 of the third embodiment stores a plurality f image observation reports that include past reports of a single patient.

Figure 12:
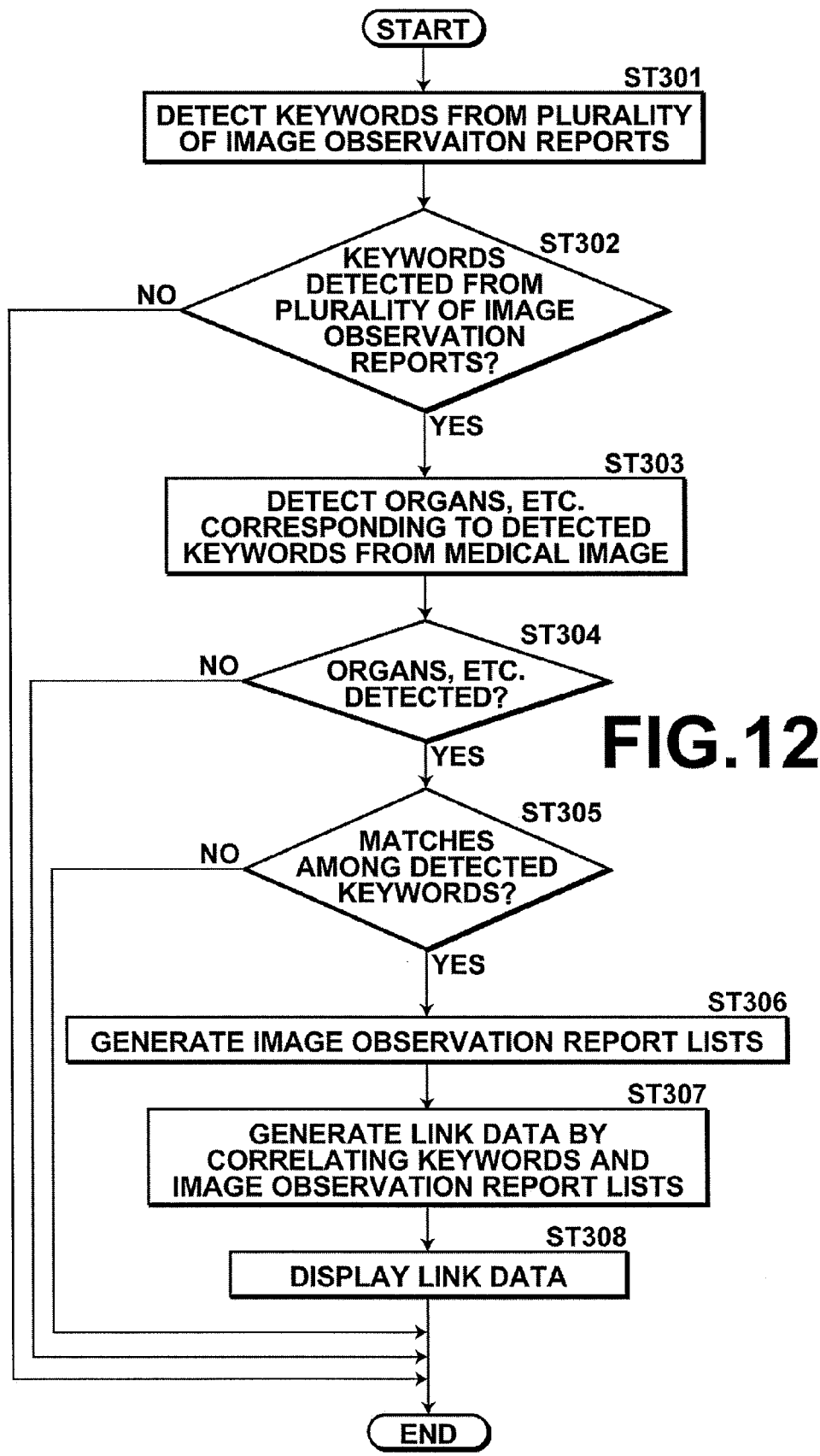
FIG. 12 is a flow chart that illustrates a medical image information display process performed by the third embodiment.

FIG. 12 is a flow chart that illustrates a medical image information display process performed by the third embodiment. First, keywords that match the keywords stored in the first keyword group storage means 20 are detected from within the plurality of image observation reports (step ST301). In the case that matching keywords are detected (YES at step ST302), the detected keywords are obtained as a second keyword group. At this time, image observation report specifying data that specify the image observation reports that include the detected keywords are obtained and correlated with the detected keywords. Examples of the image observation report specifying data include file names of image observation reports, and the dates on which the image observation reports were generated. In the case that no matching keywords are detected (NO at step ST302), the link data display process ends.

Next, the organs, etc. represented by the keywords stored in the first keyword group storage means 20 are detected from within a medical image using an automatic detecting technique in the same manner as in step ST103 (step ST303).

If organs, etc. are detected, data that specify a medical image 133 that the detected organs, etc. are pictured in, and organ data that represent the organs, etc. such as the coordinates of the organs, etc., are obtained in the same manner as in step ST103.

In the case that organs, etc. are not detected (NO at step ST304), the link data display process ends. In the case that organs, etc. are detected (YES in step ST304), keywords that represent the detected organs, etc. are obtained as a third keyword group. The keywords of the second keyword group and the keywords of the third keyword group are compared. In the case that there are no matching keywords between the second keyword group and the third keyword group (NO in step ST305), the link data display process ends. In the case that keywords that match between the second keyword group and the third keyword group are present (YES in step ST305), the link data generating means 60 obtains the matching keywords as common keywords in the same manner as in step ST106.

In the case that the common keywords are detected from within a plurality of image observation reports, the link data generating means 60 generates an image observation report list 160 (step ST306).

Figure 13:
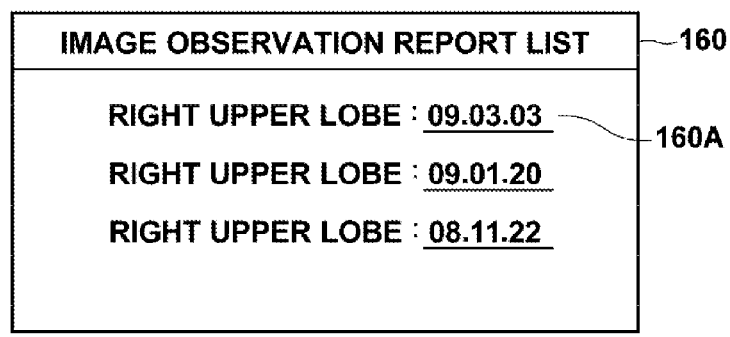
FIG. 13 is a diagram that illustrates an example of an image observation report list displayed by the second embodiment.

As illustrated in FIG. 13, the image observation report list 160 is a list in which a single common keyword is correlated with image observation report specifying data of image observation reports in which the keyword was detected. In the example of FIG. 13, dates 160A on which image observation reports were generated are correlated as image observation specifying data to a single common keyword "right upper lobe". However, the items within the image observation report list are not limited to those described above. Phrases that precede and follow the keyword that corresponds to the common keyword 150A within the image observation report may be extracted and correlated, in addition to the image observation report specifying data. It is desirable for the image observation report specifying data 160A to be listed in the image observation report list 160 in order from the most recently generated to the oldest image observation report.

Note that there may be cases in which a keyword corresponding to a single common keyword 150A is described at a plurality of locations within an image observation report. In these cases, it is desirable for information regarding the locations at which the keyword corresponding to the single common keyword 150A are described in the image observation report to be displayed correlated with the image observation report list 160. Specifically, it is desirable for indications, such as "Right Upper Lobe (common keyword): 09.03.03 (image observation report specifying data): 130 (a number indicates the number of words prior to the common keyword within the image observation report)", to be displayed for each location that the keyword is described within the image observation reports in a selectable manner in the image observation report list 160. In addition, the number of organs, etc. corresponding to the single common keyword 150A detected within medical images may also be displayed in the list.

The link data generating means 60 generates link data including the common keywords and organs, etc. detected within medical images (step ST307). At this time, image observation report lists are further correlated only to common keywords for which the image observation report lists have been generated. The link data are generated in the same manner as in step ST106 of FIG. 4 with respect to common keywords, for which image observation reports lists have not been generated.

Next, the list display means 100 obtains image observation report list data from the link data generating means 60 if the image observation report lists 160 have been generated, and displays the image observation report lists 160 within the medical image 133 (step ST308). The link data display means 70 displays indicia that represent organs, etc., and image observation report lists 160 in a manner correlated to common keywords, for which the image observation report lists 160 have been generated. Here, "display . . . in a manner correlated to" refers to a manner of display that enables correlations among the common keywords and the indicia that represent the organs, etc. to be recognized.

Indicia that represent the regions of organs, etc. corresponding to common keywords are displayed in a manner correlated to the common keywords, with respect to common keywords for which the image observation report lists 160 have not been generated, in the same manner as in step ST107. The link data display means 70 displays the image observation report specifying data 160A listed in the image observation report lists such that they are linked to the common keywords within the corresponding image observation reports with hyperlinks. Accordingly, the common keywords within specific image observation reports can be easily displayed, by specifying the image observation report specifying data 160A listed in the image observation report lists. Here, the third embodiment may be applied to the second embodiment. For example, in the case that the link data display means 70 displays a common keyword list as in the second embodiment, the display as described in the second embodiment may be performed with respect to the common keywords of the common keyword list 150 for which image observation report lists 160 have not been generated, and the image observation report list 160 may be displayed for common keywords of the common keyword list 150 for which image observation report lists 160 have been generated, in response to specification of the common keywords.

Note that in the case that a keyword corresponding to a single common keyword is described at a plurality of locations within an image observation report, the image observation report may be displayed such that the entirety thereof can be referred to, with the first instance that the corresponding keyword appears within the image observation report being displayed such that it is distinguishable from other text, in response to specification of the common keyword. Alternatively, comments that include the keyword that corresponds to the common keyword and phrases that precede and follow the keyword may be extracted from each location that the keyword is described at, and the comments may be displayed as a list from among which selection is possible, in a separate window. In this case, the image observation report may be displayed such that the entirety thereof can be referred to, with a selected comment that includes the common keyword being displayed such that it is distinguishable from other text, in response to specification of a common keyword within the comments that include the common keywords.

By adopting this configuration, in the case that keywords that represent organs, etc. are described in a plurality of image observation reports, the plurality of image observation reports can be easily referred to, and efficient diagnosis becomes possible.

In addition, in the case that the image observation specifying data are displayed in the image observation report list, it will become easy to diagnose the progression of disease in organs, etc., by specifying which image observation report information regarding the organs, etc. is described in. For example, in the case that the date that the reports were generated are displayed within the medical image, accurate diagnosis can be performed, taking the passage of time since the date that the report was generated into consideration. In addition, in the case that the image observation report specifying data are listed in the image observation report list in order from the most recently generated to the oldest image observation report, information within image observation reports regarding the same common keywords along the passage of time can be easily referred to, and efficient diagnosis becomes possible.

In the case that comments that include keywords from a plurality of image observation reports are displayed on the image observation report list, more detailed information regarding the organs, etc. can be obtained from medical images, and image observation will be facilitated. In addition, there is a high probability that phrases that precede and follow text that represents organs, etc. in the image observation report describe the organs, etc. Therefore, it is considered that there is a high probability that information that aids in understanding of the organs, etc. will be displayed, if the phrases that precede and follow the keyword within the image observation report that correspond to the common keyword are displayed.

As a modification of the third embodiment, the link data generating means 60 correlates common keywords with the organs, etc. corresponding thereto and to image observation report specifying data that represents the most recent corresponding image observation report in the case that the same common keywords are detected form within a plurality of image observation reports, instead of generating the image observation report list (step ST306). In this modification, the link data display means 70 may display the common keywords linked to keywords within the most recent image observation report by hyperlinks. In this case, when a common keyword within the medical image is specified, the keyword described in the mot recent image observation report is displayed. Therefore, the keyword described in the most recent image observation report and the entirety of the most recent image observation report can be easily referred to. In the case that the same common keywords are detected form within a plurality of image observation reports, there is a high probability that information in the most recent image observation report most correctly represents the present state of organs, etc. Therefore, accurate diagnosis becomes possible.

Figure 14:
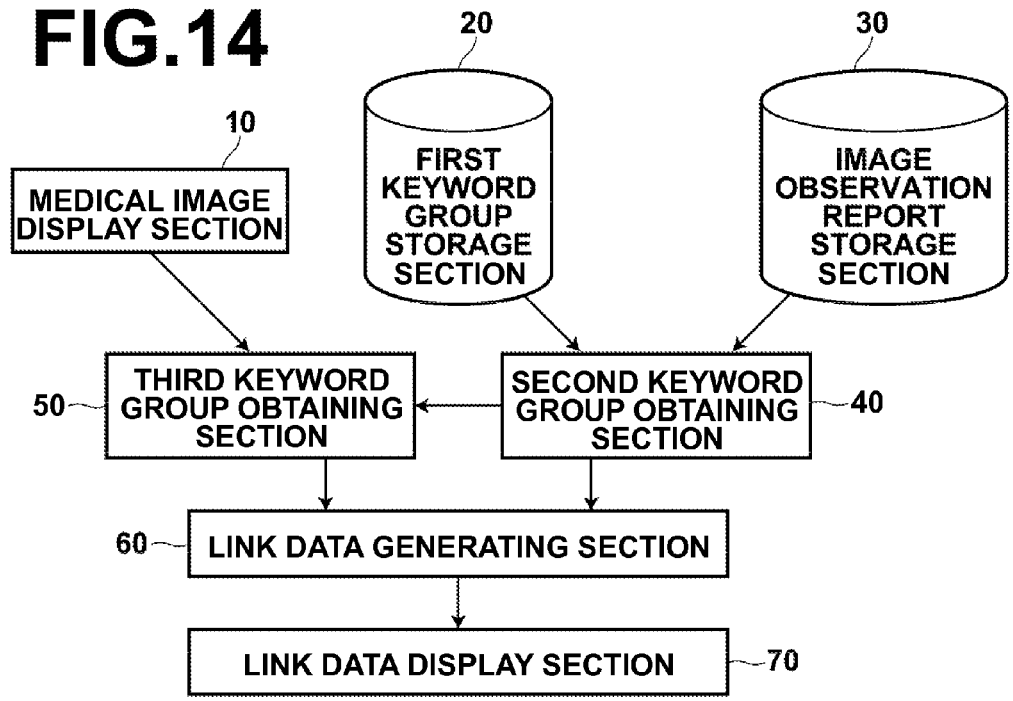
FIG. 14 is a functional block diagram that illustrates the medical image information display functions of a fourth embodiment.

A fourth embodiment of the present invention will be described with reference to FIGS. 14 and 15. FIG. 14 is a functional block diagram that illustrates the medical image information display functions of the fourth embodiment.

In the fourth embodiment, the third keyword group obtaining means 50 detects organs, etc. represented by the keywords obtained by the second keyword group obtaining means 40, instead of organs, etc. represented by the keywords stored in the first keyword group storage means. The other means illustrated in FIG. 14 are the same as those illustrated in FIG. 3, and therefore, detailed descriptions thereof will be omitted.

FIG. 15 is a flow chart that illustrates a medical image information display process performed by the fourth embodiment. Steps ST401 and ST402 are the same as steps ST101 and ST102. Therefore, only step ST403 and the steps following thereafter will be described.

The third keyword group obtaining means 50 detects organs, etc. represented by the keywords by the keywords obtained by the second keyword group obtaining means 40 from within a medical image using an automatic detecting technique (step ST403).

If organs, etc. are detected, data that specify the medical image 133 that the detected organs, etc. are pictured in, and organ data that represent the organs, etc. such as the coordinates of the organs, etc., are obtained in the same manner as in step ST103.

In the case that organs, etc. are not detected (NO at step ST404), the link data display process ends. In the case that organs, etc. are detected (YES in step ST404), keywords that represent the detected organs, etc. are obtained as a third keyword group. The link data generating means 60 generates link data that include the common keywords and the organs, etc. detected within the medical image in the same manner as in step ST106 (step ST405). Next, the link data display means 70 obtains the link data from the link data generating means 60, and displays an indicium 135A that indicates the position of an organ, etc. and a common keyword 135B in a correlated manner on the medical image 133 in the same manner as in step ST107 (step ST406).

As described above, the third keyword group obtaining means 50 detects the organs, etc. represented by the keywords obtained by the second keyword group obtaining means 40 from within the medical images, instead of those represented by keywords in the first keyword group. Therefore, the number of times that the organs, etc. are detected can be suppressed to the number of keywords obtained by the second keyword group obtaining means 40. Accordingly, processing efficiency is improved compared to a case in which organs, etc. are detected with respect to all of the keywords in the first keyword group.

A modification of the fourth embodiment will be described. The modification of the fourth embodiment is a combination of the first embodiment and the fourth embodiment. In this modification, the third keyword group detecting means 50 detects organs, etc. represented by a portion of the keywords among the keywords stored in the first keyword storage means 20, in the same manner as in the first embodiment. With respect to keywords stored in the first keyword storage means 20 other than the aforementioned portion of the keywords, organs, etc. represented by these keywords are only detected in the case that these keywords are detected as keywords included in the second keyword group, in the same manner as in the fourth embodiment.

In the modification to the fourth embodiment, organs, etc. are detected with respect to the keywords stored in the first keyword group storage means 20 other than the aforementioned portion of the keywords only if they are described in the image observation report. Therefore, processing efficiency is improved compared to a case in which organs, etc. are detected with respect to all of the keywords in the first keyword group. The number of types of pathologies is greater than the number of organs, and the burden of detecting processes for pathologies is greater than the burden of detecting processes for organs. Therefore, if keywords that represent organs are registered as the aforementioned portion of the keywords, and keywords that represent pathologies are registered as the other keywords, automatic detecting processes can be performed with respect to keywords that represent pathologies only in cases that such keywords are described within the image observation report. Accordingly, the processing burden can be effectively suppressed.

A fifth embodiment of the present invention will be described. FIG. 16 is a functional block diagram that illustrates the medical image information display functions of the fifth embodiment.

As illustrated in FIG. 16, in the fifth embodiment, the second keyword group obtaining means 40 detects keywords that represent organs, etc. which have been detected by the third keyword group obtaining means 50, instead of the keywords which are stored in the first keyword group storage means. The other elements illustrated in FIG. 16 are the same as those illustrated in FIG. 3, and therefore, detailed descriptions thereof will be omitted. In this case, only keywords that represent organs, etc. which have been automatically detected are searched for from within the image observation report and displayed. Therefore, processing efficiency is improved compared to a case in which all of the keywords in the first keyword group are searched for within the image observation report.

The present invention is not limited to the embodiments described above, and various modifications are possible, as long as they do not stray from the spirit of the invention.

What is claimed is:
1. A medical image information display apparatus, comprising:
   a display section;
   a memory;
   a processor;
   wherein, the memory comprises:
      an image observation report storage section in which image observation reports related to the medical images are stored; and
      a first keyword group storage section in which a first group of keywords that include one of keywords that represent organs and keywords that represent pathologies are stored; and
   the processor is configured to:
      obtain medial images and control the display apparatus to display the obtained medical images;
      detect phrases that match the stored first group of keywords from within the image observation reports, and obtain a second group of keywords that include the detected phrases;

automatically detect the organs and pathologies represented by the stored first group of keywords from within the medical images, and obtain a third group of keywords that include keywords corresponding to the detected organs and pathologies;

compare the second keyword group and the third keyword group, obtain common keywords that match between the two groups, and generate link data, in which each of the obtained common keywords is correlated with a corresponding one of the organs and pathologies; and control the display apparatus to display (a) the common keywords, (b) an indicia that represents the organs and pathologies corresponding to the common keywords and (c) a correlating indicia that represents a predetermined graphic and that correlates the common keywords with the indicia.

2. A medical image information display apparatus as defined in claim 1, wherein:

the processor is further configured to further correlate phrases that precede and follow the common keywords within the image observation reports to the link data in addition to the common keywords; and control the display apparatus to further display the phrases that precede and follow the common keywords in addition to the common keywords.

3. A medical image information display apparatus as defined in claim 1, wherein:

the processor is further configured to designate keywords that represent the narrowest concept as the keywords corresponding to the organs and pathologies, in the case that the same organs and pathologies are detected based on a plurality of the keywords.

4. A medical image information display apparatus as defined in claim 1, wherein:

the processor is further configured to designate phrases that represent the narrowest concept as the detected phrases, in the case that a plurality of phrases that represent the same organ are detected within the image observation reports.

5. A medical image information display apparatus as defined in claim 1, wherein:

the medical image information display apparatus further comprises an input section;

the processor is configured to:

control the display apparatus to display the image observation reports on the display section;

to specify the common keywords by accepting instructions from the input section;

to link the common keywords displayed by the link data display section to the common keywords within the image observation reports by hyperlinks; and to control the display apparatus to display the entirety of the image observation reports in response to specification of the displayed common keywords, with the specified common keywords being displayed in an emphasized manner compared to other text within the image observation reports.

6. A medical image information display apparatus as defined in claim 1, wherein:

the processor is configured to control the display apparatus to display a common keyword list that includes a plurality of common keywords and to display an indicia that represent an organ or a pathology corresponding to a specified common keyword, in response to specification of the specified common keyword from among the plurality of common keywords displayed in the common keyword list.

7. A medical image information display apparatus as defined in claim 1, wherein:

the processor is further configured to obtain the second group of keywords from a plurality of image observation reports regarding the same patient and to correlate an image observation report specifying data that specifies image observation reports that include the common keywords with the link data.

8. A medical image information display apparatus as defined in claim 7, wherein:

the processor is configured to correlate the common keywords included in the newest image observation report from among the plurality of image observation reports and image observation report specifying data that specifies the newest image observation report with the link data, when phrases corresponding to the same common keywords are detected within the plurality of image observation reports.

9. A medical image information display apparatus as defined in claim 7, wherein:

the processor is further configured to generate an image observation report list that includes image observation report specifying data that specify a plurality of image observation reports when phrases corresponding to the same common keywords are detected within the plurality of image observation reports, and to link the image observation report specifying data included in the image observation report list and the same common keywords included in the image observation reports corresponding to the image observation report specifying data by hyperlinks; and the processor is configured to control the display apparatus to display the image observation report list.

10. A medical image information display apparatus as defined in claim 1, wherein:

the processor is further configured to automatically detect the organs and pathologies represented by the second group of keywords from within the medical images, instead of those represented by the first group of keywords.

11. A medical image information display apparatus as defined in claim 1, wherein:

the processor is configured to automatically detect the organs and pathologies represented by a portion of the first group of keywords from within the medical images, only in cases that the portion of the first group of keywords match those included in the second group of keywords.

12. A medical image information display method, comprising the steps of:

obtaining and displaying medical images;

storing image observation reports related to the medical images;

storing a first group of keywords that include one of keywords that represent organs and keywords that represent pathologies;

detecting phrases that match the stored first group of keywords from within the image observation reports and obtaining a second group of keywords that include the detected phrases;

automatically detecting the organs and pathologies represented by the stored first group of keywords from within the medical images and obtaining a third group of keywords that include keywords corresponding to the detected organs and pathologies;

comparing the second keyword group and the third keyword group, obtaining common keywords that match between the two groups, and generating link data, in which each of the obtained common keywords is correlated with its corresponding one of the organs and its corresponding one of pathologies; and displaying:
(a) the common keywords,
(b) an indicia that represents the organs and pathologies corresponding to the common keywords and
(c) a correlating indicia that represents a predetermined graphic and that correlates the common keywords with the indicia.

13. A non-transitory computer readable recording medium, having recorded therein a medical image information display program that causes a computer to execute the following operations:

to obtain and to display medical images;

to store image observation reports related to the medical images;

to store a first group of keywords that include one of keywords that represent organs and keywords that represent pathologies;

to detect phrases that match the stored first group of keywords from within the image observation reports, and to obtain a second group of keywords that include the detected phrases;

to automatically detect the organs and pathologies represented by the stored first group of keywords from within the medical images, and to obtain a third group of keywords that include keywords corresponding to the detected organs and pathologies;

to compare the second keyword group and the third keyword group, to obtain common keywords that match between the two groups, and to generate link data, in which each of the obtained common keywords is correlated with its corresponding one of the organs and its corresponding one of pathologies; and to control the computer to display:
(a) the common keywords,
(b) an indicia that represents the organs and pathologies corresponding to the common keywords and
(c) a correlating indicia that represents a predetermined graphic and that correlates the common keywords with the indicia.

* * * * *